US012616466B2

(12) United States Patent (10) Patent No.: US 12,616,466 B2
Shan (45) Date of Patent: May 5, 2026

(54) CARTRIDGE ASSEMBLY, HEAD ASSEMBLY AND SURGICAL STAPLER

(71) Applicant: Touchstone International Medical Science Co., Ltd., Suzhou (CN)

(72) Inventor: Teng Shan, Suzhou (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 10 days.

(21) Appl. No.: 18/687,656

(22) PCT Filed: Aug. 31, 2022

(86) PCT No.: PCT/CN2022/116032
§ 371 (c)(1),
(2) Date: Feb. 28, 2024

(87) PCT Pub. No.: WO2023/030355
PCT Pub. Date: Mar. 9, 2023

(65) Prior Publication Data
US 2025/0134521 A1 May 1, 2025

(30) Foreign Application Priority Data

Aug. 31, 2021 (CN) .......................... 202111013470.8
Aug. 31, 2021 (CN) .......................... 202111015381.7
Aug. 31, 2021 (CN) .......................... 202122086338.1

(51) Int. Cl.
*A61B 17/072* (2006.01)
(52) U.S. Cl.
CPC .. *A61B 17/072* (2013.01); *A61B 2017/07228* (2013.01); *A61B 2017/07257* (2013.01);
(Continued)

(58) Field of Classification Search
CPC ............ A61B 17/068; A61B 17/07207; A61B 2017/07271; A61B 2017/07214–07285
See application file for complete search history.

(56) References Cited

U.S. PATENT DOCUMENTS 8,631,992 B1 * 1/2014 Hausen .............. A61B 17/0644
227/181.1
8,662,369 B1 * 3/2014 Manoux ............. A61B 17/0682
227/180.1
(Continued)

FOREIGN PATENT DOCUMENTS

CN            210931598 U        7/2020
CN            111789645 A        10/2020
(Continued)

OTHER PUBLICATIONS

International Search Report issued in PCT/CN2022/116032 on Dec. 14, 2022.

*Primary Examiner* — Linda J. Hodge
(74) *Attorney, Agent, or Firm* — Fox Rothschild LLP

(57) ABSTRACT
A cartridge assembly, a head assembly and a surgical stapler are provided. The cartridge assembly includes: a staple strip including at least one staple strip body and staples, wherein each staple is rotatably connected to the staple strip body via a connecting portion; and a cartridge cover jacketed on the staple strip body, wherein the cartridge cover includes at least one bending portion extending in an axial direction of the stapler, the bending portion is provided with a plurality of staple holes, each staple hole includes a first hole wall and a second hole wall extending in the axial direction, and the first hole wall is higher than the second hole wall. The present disclosure makes the staplers easier to be separated from the cartridge cover after being closed.

20 Claims, 36 Drawing Sheets

A1-A1

(52) U.S. Cl.
CPC .............. *A61B 2017/07271* (2013.01); *A61B*
*2017/07278* (2013.01); *A61B 2017/07285*
(2013.01)

(56) References Cited

U.S. PATENT DOCUMENTS

| | | | |
|---|---|---|---|
| 2013/0075445 A1* | 3/2013 | Balek ............... | A61B 17/07207 |
| | | | 227/176.1 |
| 2014/0263557 A1* | 9/2014 | Schaller ........... | A61B 17/07207 |
| | | | 227/176.1 |
| 2015/0230793 A1 | 8/2015 | Kostrzewski | |
| 2015/0297225 A1* | 10/2015 | Huitema .............. | A61B 17/105 |
| | | | 227/176.1 |
| 2016/0058441 A1* | 3/2016 | Morgan ............. | A61B 17/0644 |
| | | | 606/219 |
| 2018/0325514 A1 | 11/2018 | Harris et al. | |
| 2019/0000480 A1* | 1/2019 | Yee .................. | A61B 17/07207 |
| 2019/0261983 A1* | 8/2019 | Granger ........... | A61B 17/07207 |
| 2022/0313249 A1* | 10/2022 | Eisinger .............. | A61B 17/072 |

FOREIGN PATENT DOCUMENTS

| | | |
|---|---|---|
| CN | 112353443 A | 2/2021 |
| CN | 215874787 U | 2/2022 |

* cited by examiner

CARTRIDGE ASSEMBLY, HEAD ASSEMBLY AND SURGICAL STAPLER

CROSS-REFERENCE TO RELATED APPLICATIONS

This application is based upon PCT patent application No. PCT/CN2022/116032, filed on Aug. 31, 2022, which claims priority to Chinese Patent Applications No. 202111013470.8, No. 202122086338.1 and No. 202111015381.7, filed on Aug. 31, 2021, the entire contents of which are incorporated herein by reference.

TECHNICAL FIELD

The present disclosure relates to surgical instruments' technology, more particularly, to a cartridge assembly, a head assembly and a surgical stapler.

BACKGROUND

In the prior art, the surgical stapler generally includes an instrument platform, a firing handle rotatably connected to the instrument platform and a head assembly mounted on the instrument platform. The head assembly can be inserted through a small incision on the body using a trocar to approach the surgical site for surgery. The head assembly includes a cartridge assembly and an anvil located relative to each other. The cartridge assembly includes a staple strip, a support member supporting the staple strip, and a cartridge cover accommodating the staple strip and the support member. A firing member is provided on a proximal side of the cartridge cover. During a process of firing the surgical stapler, a cutter is pushed to move distally by a cutter pushing rod, then the cutter drives the firing member to move distally, so the firing member pushes staples rotatably connected to a staple strip body outwards, a cutting portion of the firing member separates the staples from the staple strip body, the cutter cuts off the tissue located between cartridge assembly and the anvil, to complete the process of firing the stapler.

In the existing cartridge assembly, an upper plate of the cartridge cover forms staple holes corresponding to the staples. However, as the upper plate of the cartridge cover is high, after the staples are closed, the staples may fail to be completely separated from the cartridge cover, which affects the surgical effect.

In the present disclosure, the terms "distal side" and "proximal side" are used herein with reference to an operator manipulating the surgical stapler. The term "proximal side" refers to a side closer to the operator, and the term "distal side" refers to a side away from the operator, that is, a side closer to the surgical site. In the stapler, "inner side" and "outer side" are defined with respect to the axis of the stapler, "inner side" is the side close to the axis, and "outer side" is the side far from the axis.

SUMMARY

To solve the problems in the prior art, the present disclosure aims to provide a cartridge assembly, a head assembly and a surgical stapler, wherein the staples are easier to be separated from the cartridge cover after the staplers are closed.

In the present disclosure, a cartridge assembly is provided, wherein the cartridge assembly includes: a staple strip including at least one staple strip body and a plurality of staples, wherein each staple is rotatably connected to the staple strip body via a connecting portion; a cartridge cover jacketed on the staple strip body, wherein the cartridge cover includes at least one bending portion extending in an axial direction, the bending portion is provided with a plurality of staple holes, each staple hole includes a first hole wall and a second hole wall extending in the axial direction, and the first hole wall is higher than the second hole wall in a height direction.

In the present disclosure, a head assembly including an anvil and the cartridge assembly is provided, wherein a surface of the anvil facing the cartridge assembly is an anvil surface, and an anvil cutting slot is provided in the anvil, the anvil surface is provided with an anvil convex portion protruding towards the cartridge assembly on at least one side of the anvil cutting slot; a cartridge cutting slot is provided in the cartridge assembly and the bending portion is provided on one side of the cartridge cover close to the cartridge cutting slot.

In the present disclosure, a surgical stapler including the cartridge assembly or the head assembly is provided.

The cartridge assembly, the head assembly and the surgical stapler have the following advantages.

The present disclosure provides a cartridge assembly used for a surgical assembly, wherein the staple holes are located on the bending portion of the cartridge cover, the second hole wall is lower than the first hole wall, the staple hole partially recesses in the height direction, so that the staples are easier to be separated from the cartridge cover after being closed and formed; furthermore, more tissue can be accommodated in openings of the staple holes for the staples, the staples are easier to puncture the tissue and be formed, thereby improving the surgery effect.

BRIEF DESCRIPTION OF THE DRAWINGS

By reading the detailed description of non-limiting embodiments with reference to the following drawings, other features, objectives, and advantages of the present disclosure will become more apparent.

DETAILED DESCRIPTION

Figure 1:
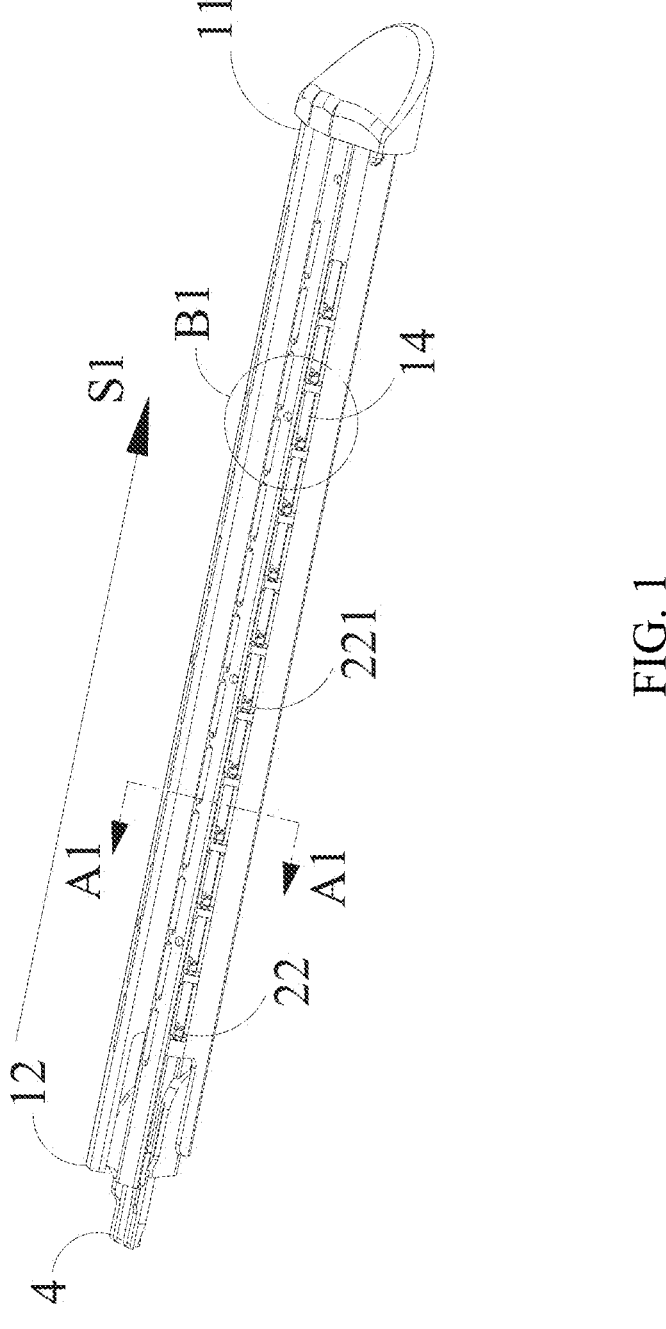
FIG. 1 is a structural schematic view of a cartridge assembly according to a first embodiment of the present disclosure.

The exemplary embodiments will be more comprehensively described by combining the drawings. However, the exemplary embodiments can be implemented in multiple forms and should not be limited to the embodiments described herein. On the contrary, providing these embodiments will make the present disclosure comprehensive and complete, and will comprehensively convey the concept of the exemplary embodiments to those skilled in the art. The same reference numbers in the drawings represent the same or similar structures, so repeated descriptions of them will be omitted.

The present disclosure provides a cartridge assembly and a surgical stapler including the same. The surgical stapler includes an instrument platform, a firing handle rotatably connected to the instrument platform and a head assembly mounted on the instrument platform. The head assembly includes a cartridge assembly and an anvil located relative to each other. The cartridge assembly includes: a staple strip including at least one staple strip body and a plurality of staples, wherein each staple is rotatably connected to the staple strip body via a connecting portion; and a cartridge cover jacketed on the staple strip body, wherein the cartridge includes at least one bending portion extending along an axial direction of the stapler, each bending portion is provided with a plurality of staple holes. The staple hole includes a first hole wall and a second hole wall extending along the axial direction, and the first hole wall is higher than the second hole wall in a height direction, allowing more tissue to enter openings of the staple holes for the staples during surgery, The staples are easier to puncture the tissue and be formed, and at the same time, the staple hole partially recesses in the height direction, making the staples easier to be separated from the cartridge cover after being closed, improving the surgical effect.

In the following, the structures of the cartridge assembly in specific embodiments are described by combining the drawings. It should be understood that the specific structures of the embodiments are only exemplary, and are not intended to be a limitation to the protection scope of the present disclosure.

FIGS. 1-9 are structural schematic views of the cartridge assembly according to a first embodiment of the present disclosure. The cartridge assembly includes: a staple strip 2, a support member 3 for supporting the staple strip 2, and a cartridge cover 1 for accommodating the staple strip 2 and the support member 3. The staple strip 2 includes at least one staple strip body 21 and a plurality of staples 22, each staple 22 is rotatably and separably connected to the staple strip body 21 via a connecting portion 221. The cartridge cover 1 is jacketed on the staple strip body 21, and at least partially covers an upper surface of the staple strip body 21. A firing member 4 is provided at a proximal side of the cartridge assembly, and the firing member 4 is located at the bottom of the cartridge cover 1 and can move along the axis direction. In an initial state, the firing member 4 is located at a proximal side of the cartridge assembly. During the process of firing the surgical stapler, the firing member 4 moves towards a distal side of the cartridge assembly, contacts the staples 22, drives the staples 22 to rotate and be closed at the anvil, and separates the staples 22 from the staple strip body 21 and the cartridge cover 1. In this embodiment, there are two support members 3, two staple strips 2, and two cartridge covers 1. The staple strips 2 are respectively set on the corresponding support members 3, and staples 22 are set on both sides of the staple strips 2. The cartridge cover 1 is jacketed on the support members 3 and the staple strips 2, that is, the two staple strips 2 and the two support members 3 are symmetrically set relative to the axial direction. In other alternative embodiments, the number of supporting members 3, staple strips 2, and cartridge cover 1 can be changed as needed, not limited to those shown in the drawings, for example, the staple strips 2 can also be provided with staples 22 on only one side, all of which fall within the protection scope of the present disclosure. In this embodiment, during a process of rotating the staple 22, at least a part of the side wall of the staple 22 simultaneously abuts the support member 3 and an inner wall of the side plate of the cartridge cover 1, so that the side wall of the staple 22 is always limited, maintaining that the staple 22 does not shift inward or outward when being rotated.

As shown in FIGS. 1 to 6, the cartridge cover 1 includes a bending portion 18 extending along the axial direction. The bending portion 18 is provided with a plurality of staple holes 14. Each staple hole 14 includes a first hole wall 141 and a second hole wall 142 extending along the axial direction. The first hole wall 141 and the second hole wall 142 are located on different planes. Specifically, the first hole wall 141 is located on the upper plate of the cartridge cover 1, and the second hole wall 142 is located on the side plate of the cartridge cover 1. The first hole wall 141 is higher than the second hole wall 142 in the height direction, so the staple hole 14 partially recesses in the height direction, and extends from the upper plate of the cartridge cover 1 to the side plate of the cartridge cover 1. At this time, the staple hole 14 is three-dimensional, so that a larger exposing space of the cartridge cover 1 is formed, that is, the staple hole 14 recesses downwards to the side plate of the cartridge cover 1. In this way, the staple 22 has more exposing space, the tissue can fully enter the area surrounded by the contour of the staple 22 when the staple 22 is being closed. The staple 22 can better puncture the tissue and achieve anastomosis, while the staple 22 can be easier to pass upwards through the staple hole 14 and be separated from the cartridge cover 1 after being closed.

Figure 3:
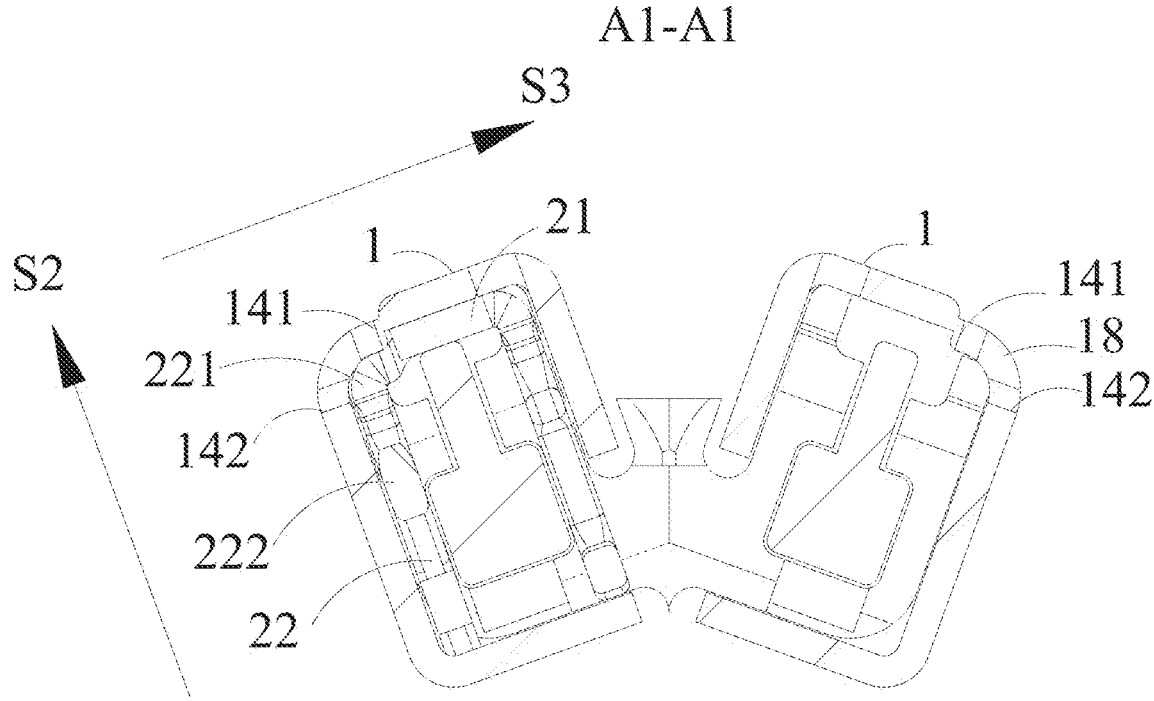
FIG. 3 is a cross-sectional view of A1-A1 direction of FIG. 1.
Figure 4:
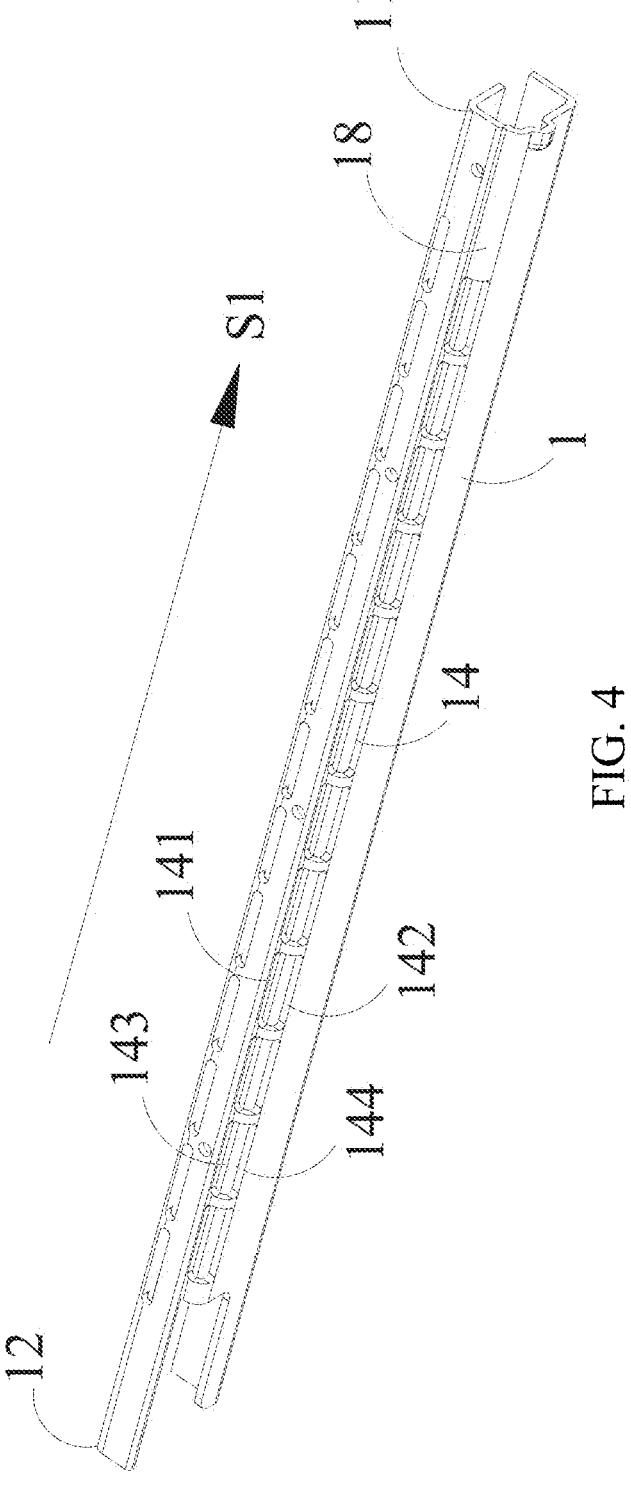
FIG. 4 is a structural schematic view of a cartridge cover according to the first embodiment of the present disclosure.
Figure 5:
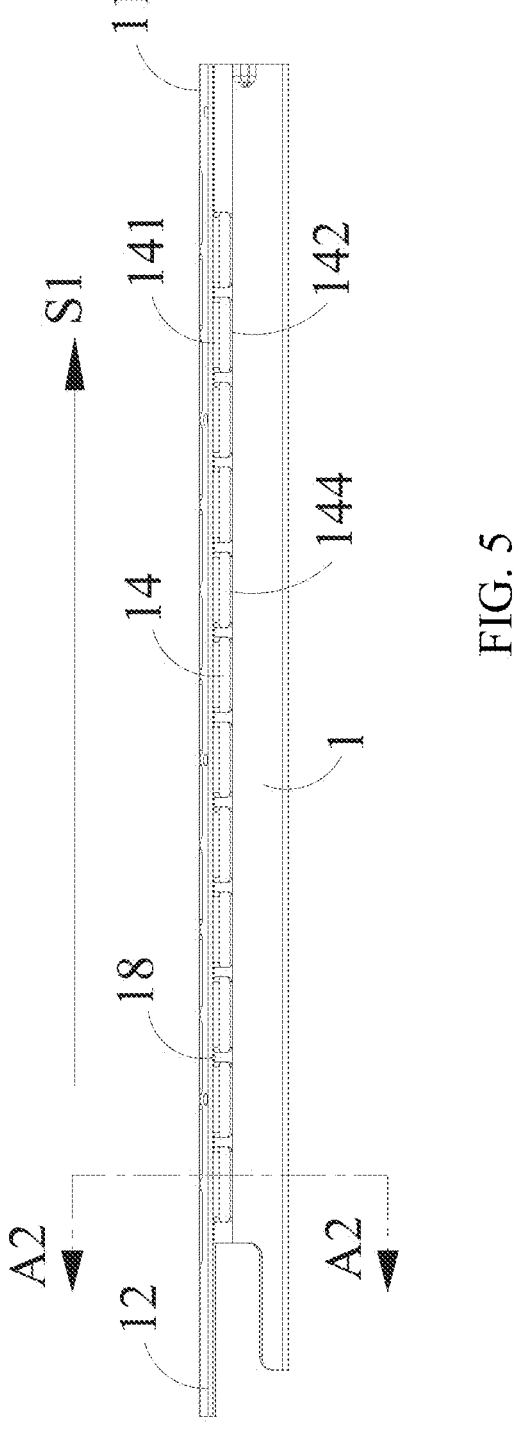
FIG. 5 is a front view of the cartridge cover according to the first embodiment of the present disclosure.
Figure 6:
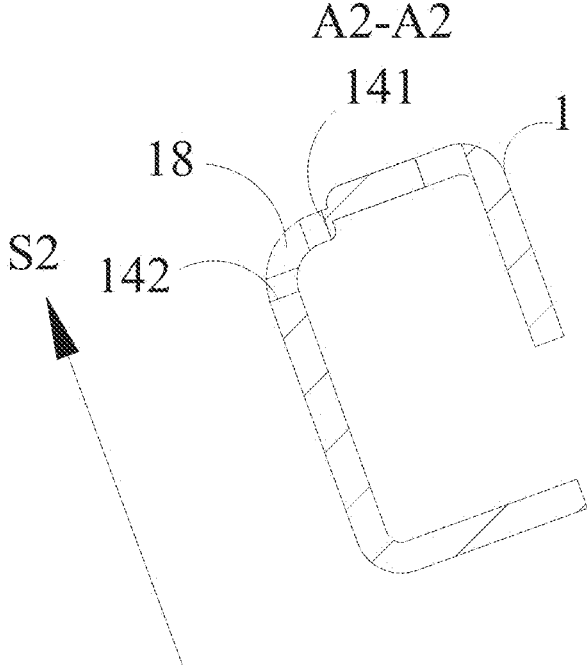
FIG. 6 is a cross-sectional view of A2-A2 direction of FIG. 5.
Figure 10:
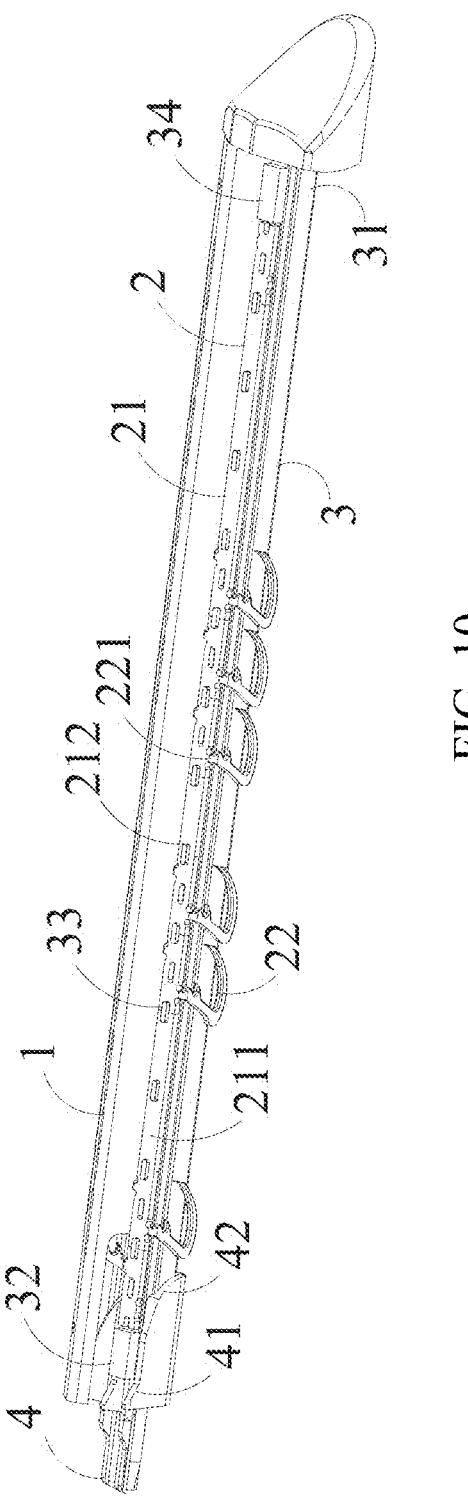
FIG. 10 is a structural schematic view of the cartridge assembly omitting the cartridge cover on one side according to a second embodiment of the present disclosure.
Figure 22:
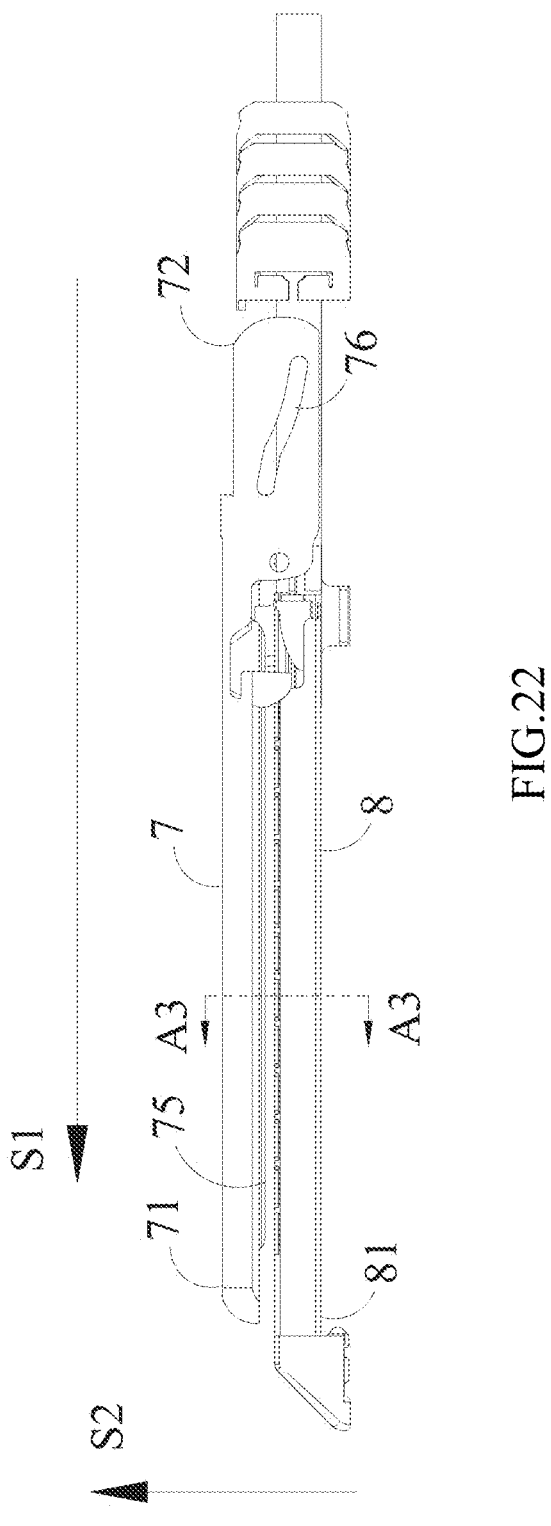
FIG. 22 is a structural schematic view of the head assembly in a second state according to the seventh embodiment of the present disclosure.
Figure 25:
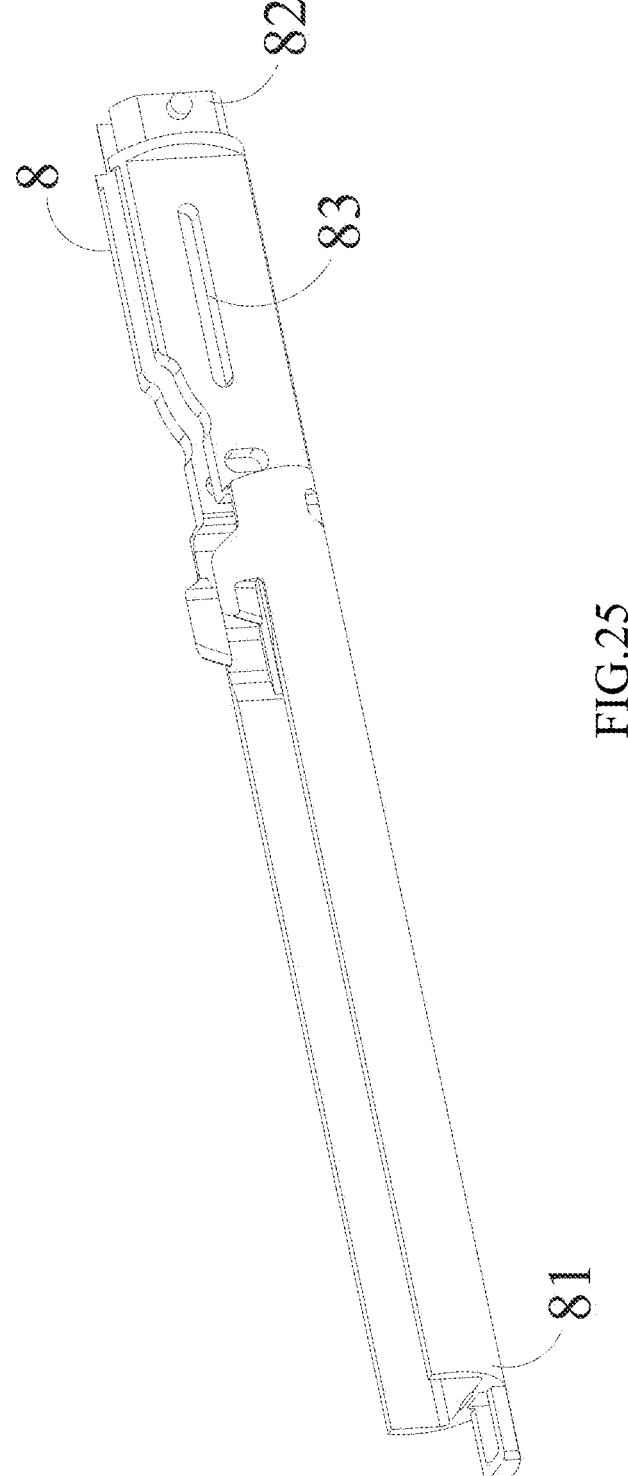
FIG. 25 is a structural schematic view of a cartridge frame according to the seventh embodiment of the present disclosure.

In the present disclosure, the terms "distal side" and "proximal side" are used herein with reference to an operator manipulating the surgical stapler. The term "proximal side" refers to a side closer to the operator, and the term "distal side" refers to a side away from the operator, that is, a side closer to the surgical site. The direction along the axis of the stapler is the axial direction, i.e., from a distal side to a proximal side of the stapler or from the proximal side to the distal side of the stapler. For example, in the perspective of FIG. 1, the distal side 11 of the cartridge cover 1 is the right side, and the proximal side 12 of the cartridge cover 1 is the left side. In the perspective of FIG. 10, the distal side 31 of the support member 3 is the right side and the proximal side 32 of the support member 3 is the left side. In the present disclosure, for a component, the inner and outer sides are defined with respect to its axis, wherein the side close to the axis is the inner side and the side away from the axis is the outer side. In the present disclosure, the S1 direction in FIG. 1 is the direction from the proximal side to the distal side of the stapler, and the S1 direction or the direction opposite to the S1 direction is defined as the axial direction of the stapler. The S2 direction shown in FIGS. 3 and 6 is defined as the height direction, that is, the longitudinal direction. The upper plate of the cartridge cover 1 is located above the staple strip body 21. The S3 direction in FIG. 3 is defined as the width direction, that is, the horizontal direction. Each of the left and right sides of the upper plate of the cartridge cover 1 is connected to the side plate via a bending portion 18, and the staples 22 are located on the left and right sides of the staple strip body 21. In the perspective of FIG. 22, the distal side 71 of the anvil 7 is the left side and the proximal side 72 of the anvil 7 is the right side. In the perspective of FIG. 25, the distal side 81 of the staple frame 8 is the left side and the proximal side 82 of the staple frame 8 is the right side.

Figure 2:
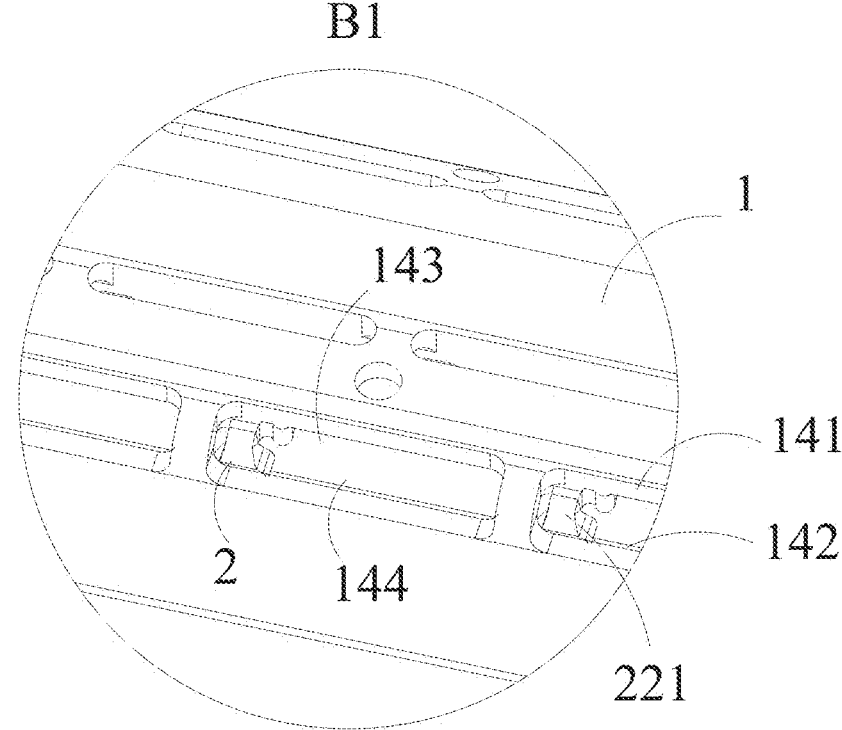
FIG. 2 is an enlarged view of B1 area in FIG. 1.

As shown in FIGS. 1-3, the bending portion 18 is connected between the upper plate and one side plate of the cartridge cover 1. The staple hole 14 includes a first section 143 and a second section 144 connected to each other. The first section 143 of the staple hole 14 is located on the upper plate of the cartridge cover 1, and the second section 144 of the staple hole 14 is located on the side plate of the cartridge cover 1. The first hole wall 141 is located on a side of the first section 143 away from the second section 144 of the staple hole 14, and the second hole wall 142 is located on a side of the second section 144 away from the first section 143 of the staple hole. The first hole wall 141 is parallel to a surface of the side plate of the cartridge cover 1, and the second hole wall 142 is parallel to a surface of the upper plate of the cartridge cover 1. In this embodiment, the highest point of the connecting portion 221 of the staple 22 is lower than the highest point of the first hole wall 141 of the staple hole 14 in the height direction. The highest point of the connecting portion 221 will not protrude from the upper plate of the cartridge cover 1. Therefore, when the stapler is not fired, the connecting portion 221 will not contact with the tissue. The lowest point of the connecting portion 221 of the staple 22 is lower than the highest point of the second hole wall 142 of the staple hole 14 in the height direction, so that in the initial state, the connecting portion 221 will not be completely exposed outside the staple hole 14, improving the stability of the staple 22 in the staple hole 14 when the stapler is not fired.

As shown in FIG. 3, in this embodiment, a projection of the connecting portion 221 on the side plate of the cartridge cover 1 at least partially coincides with that of the staple hole 14 on the side plate of the cartridge cover 1. When the stapler is fired, the staple 22 is more easily separated from the cartridge cover 1 after being closed and formed. Taking FIG. 3 as an example, the projection of the connecting portion 221 on the left panel of the cartridge cover 1 at least partially coincides with that of the staple hole 14 on the left panel of the cartridge cover 1.

Figure 7:
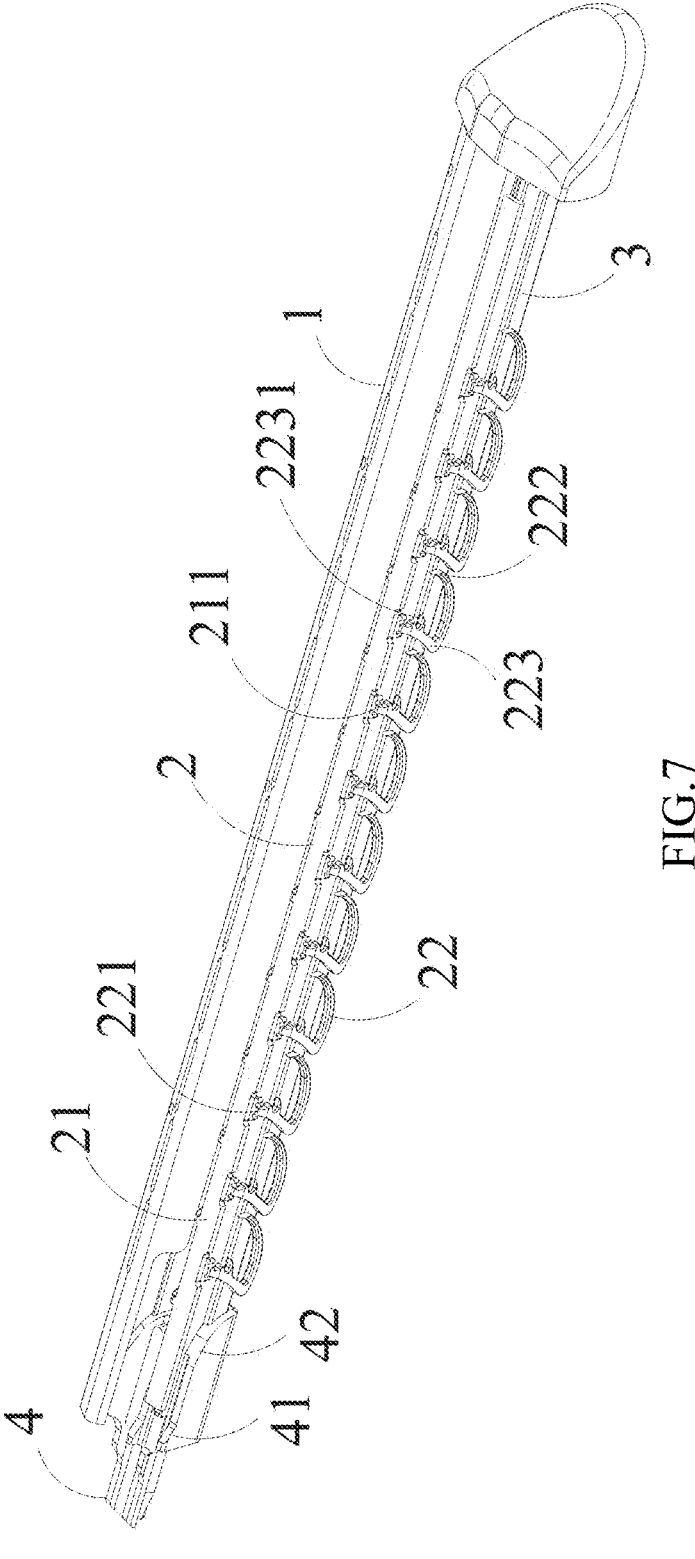
FIG. 7 is a structural schematic view of the cartridge assembly omitting the cartridge cover on one side according to the first embodiment of the present disclosure.

As shown in FIGS. 1-3, in this embodiment, a highest point of a staple leg 222 of the staple 22 is lower than the lowest point of the second hole wall 142 of the staple hole 14 in the height direction. Therefore, when the stapler is not fired, the staple leg 222 of the staple 22 will not be exposed outside the staple hole 14, so the staple leg 222 of the staple 22 is prevented from scratching the tissue. As shown in FIG. 7, the staple 22 further includes a crown portion 223 connected to the connecting portion 221. The side of the crown portion 223 facing the distal direction is provided with a barb 2231. In the initial state, the second hole wall 142 is higher than the barb 2231 to prevent the barb 2231 from exposing outside the staple hole 14 and scratching the tissue.

As shown in FIG. 3, the distance between the first hole wall 141 and the second hole wall 142 of the staple hole 14 in the lateral direction (S3 direction) is greater than the distance between two sides of the staple 22 in the lateral direction, that is, the width of the staple hole 14 is greater than the width of the staple 22, so the staple 22 can completely pass through the staple hole 14 without being stuck when the stapler is being fired. Preferably, a projection of the staple 22 on the upper plate of the cartridge cover 1 falls within a coverage range of a projection of the staple hole 14 on the upper plate of the cartridge cover 1. When the firing member 4 drives the staple 22 to move upwards, the staple 22 can pass through the staple hole 14 more smoothly without being obstructed by the wall of the staple hole 14 or getting stuck inside the staple hole 14.

As shown in FIG. 6, the cartridge cover 1 includes two bending portions 18 located on both sides of the staple strip 2, that is, in the perspective of FIG. 6, one bending portion 18 is provided on the left side of the upper plate of the cartridge cover 1, and the other bending portion 18 is provided on the right side of the upper plate of the cartridge cover 1. One bending portion 18 connects the upper plate and the left side plate of the cartridge cover 1, while the other bending portion 18 connects the upper plate and the right side plate of the cartridge cover 1. The surface of the bending portion 18 is a smooth circular arc surface. In this embodiment, it is only illustratively shown that the staple holes 14 are provided in the bending portion 18 on one side of the cartridge cover 1. Another type of staple holes are set at the position close to the right side plate on the upper plate of the cartridge cover 1, which are completely located on the upper plate of the cartridge cover 1. In another alternative implementation, the staple holes 14 can be provided on each of the two bending portions 18, that is, the staple holes at the position close to the right plate on the upper plate of the cartridge cover 1 are simultaneously located on the upper plate and the right side plate of the cartridge cover 1, the two rows of staple holes 14 set in the cartridge cover 1 are symmetrical with respect to the centerline of the cartridge cover 1.

Figure 8:
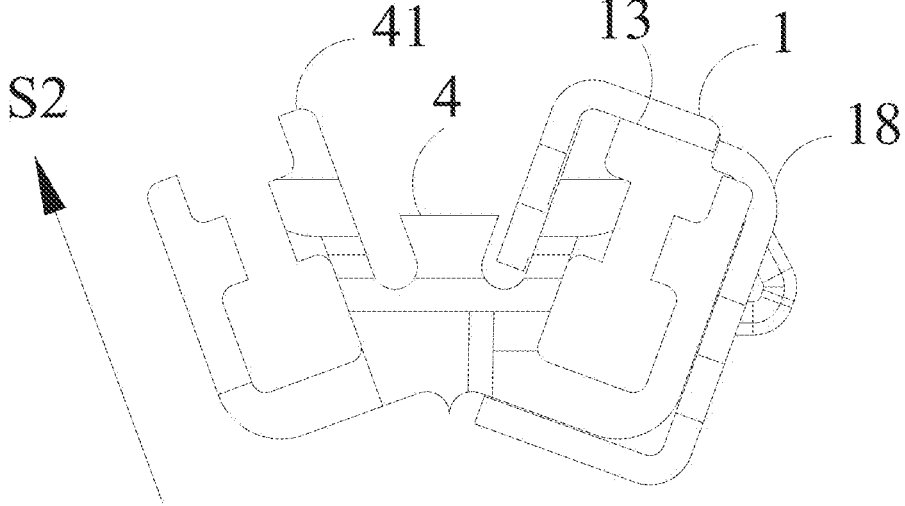
FIG. 8 is a side view of the cartridge assembly omitting the cartridge cover on one side according to the first embodiment of the present disclosure.
Figure 9:
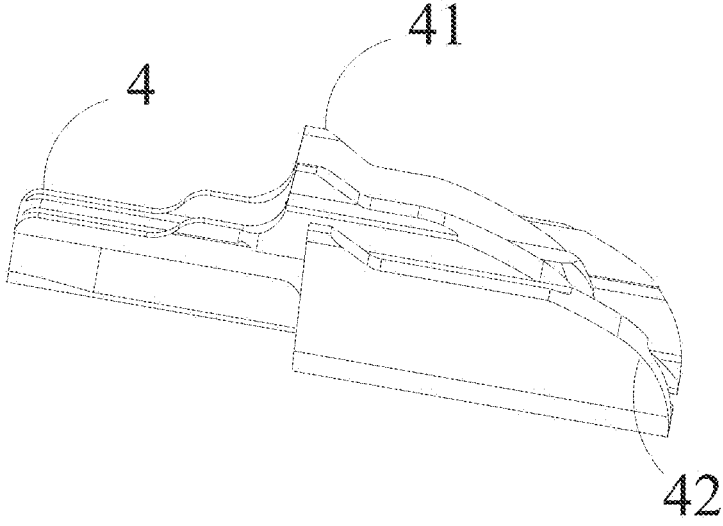
FIG. 9 is a structural schematic view of a firing member according to the first embodiment of the present disclosure.

As shown in FIGS. 7-9, the inner surface of the cartridge cover 1 fits the upper surface of the staple strip body 21. The firing member 4 includes a staple pushing portion 42 and a cutting portion 41. When the stapler is fired, the firing member 4 moves in the S1 direction from the proximal side of the cartridge assembly to the distal side of the cartridge assembly. The staple pushing portion 42 of the firing member 4 first contacts the crown portion 223 of the staple 22, and drives the staple leg 222 of the staple 22 to rotate around the connecting portion 221, the staple leg 222 extends upwards from the staple hole 14, then the staple 2 is closed into a D-shape under the action of the anvil. The cutting portion 41 cuts the connecting portion 221, and the staple 22 can be separated from the staple strip body 21, move upwards through the staple hole 14 and be closed on the tissue, then the staple 22 is separated from the cartridge cover 1.

Figure 11:
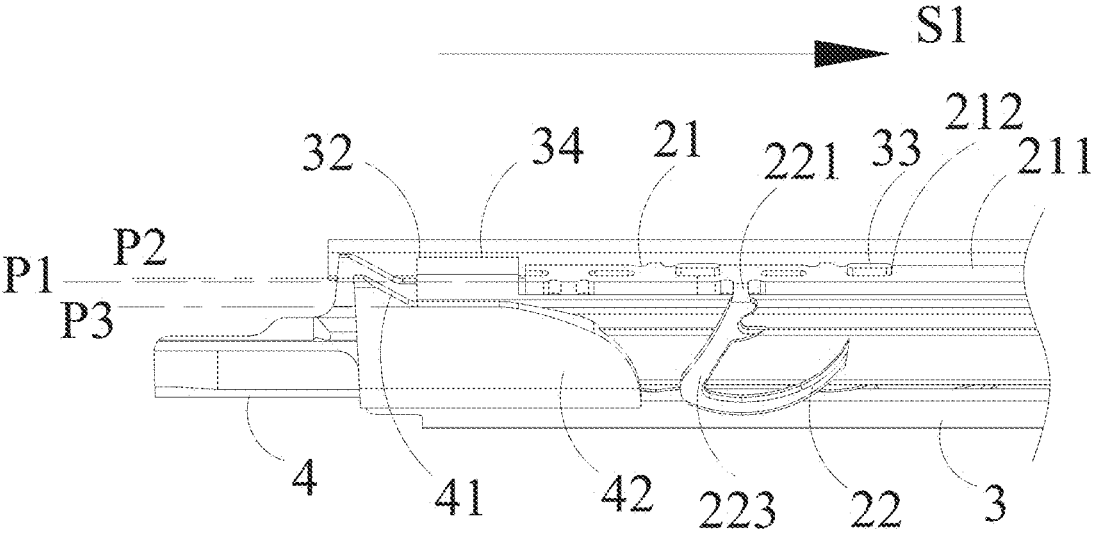
FIG. 11 is a partial structural schematic view of the staple strip cooperating with the firing member according to the second embodiment of the present disclosure.
Figure 12:
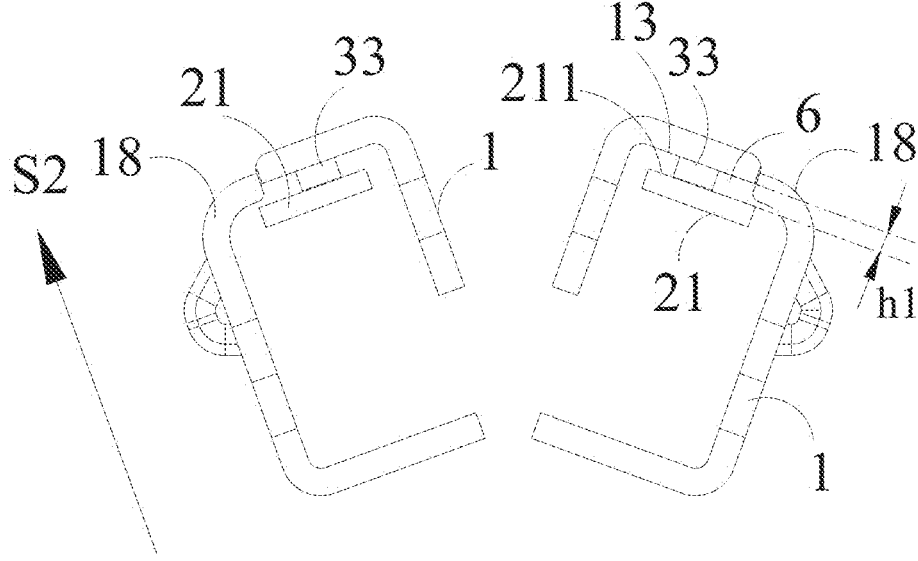
FIG. 12 is a structural schematic view of the cartridge cover cooperating with the staple strip body according to the second embodiment of the present disclosure.

FIGS. 10-12 are structural schematic views of the cartridge assembly according to a second embodiment of the present disclosure. The difference between this embodiment and the first embodiment is that a first gap 6 is formed between the upper surface of the staple strip body 21 and the surface of the cartridge cover 1 arranged relative to the upper surface of the staple strip body 21. The first surface 211 (i.e., the upper surface of the staple strip body 21) is defined as a surface on one side of the staple strip body 21 that is away from the support member 3. The second surface 13 (i.e., the inner surface of the upper plate of the cartridge cover 1) is defined as a surface on one side of the cartridge cover 1 that is arranged relative to the first surface 211 of the staple strip body 21. The first gap 6 is formed between the first surface 211 and the second surface 13.

In FIG. 12, the staple strip body 21 is represented as a square frame, and the main structure of the support member 3 is omitted. Only the cooperation relationship between the first cartridge convex portion 33, the staple strip body 21, and the cartridge cover 1 is shown as an example. A first gap 6 is formed between the first surface 211 of the staple strip body 21 and the second surface 13 of the cartridge cover 1, and a height from an upper surface to a bottom surface of the first gap 6 is h1. The height h1 of this first gap 6 can vary depending on the size of the cartridge assembly. As shown in FIG. 11, P1 is a line indicating the position of the highest point of the cutting portion 41 in the height direction. P2 is a line indicating the position of the first surface 211 of the staple strip body 21 in the height direction. P1 is higher than P2, facilitating driving the cutting portion 41 of the firing member 4 to separate the staples 22 from the staple strip 2. This ensures that when the stapler is being fired, the firing member 4 can push the staples 22 out and towards the anvil, so the staple 22 can be closed on the tissue.

In this embodiment, the highest point of the cutting portion 41 of the firing member 4 abuts the second surface 13 of the cartridge cover 1, and the cutting portion 41 of the firing member 4 can maximize the use of the first gap 6 to separate the staple 22 from the staple strip 2. As shown in FIG. 11, in this embodiment, P3 is a line indicating the position of the lowest point of the cutting portion 41 of the firing member 4 in the height position, and P3 is lower than P2. The cutting portion 41 of the firing member 4 is configured to be at least partially aligned with the connecting portion 221 in the axial direction, so that the staples 22 are completely separated from the staple strip body 21 and closed on the tissue after the stapler is fired.

As shown in FIGS. 10-12, in this embodiment, the surface of the support member 3 is provided with at least one first cartridge convex portion 33. A surface of the first cartridge convex portion 33 away from the support member 3 (i.e., the upper surface of the first cartridge convex portion 33) is higher than the first surface 211 of the staple strip body 21 in the height direction, and the upper surface of the first cartridge convex portion 33 abuts the second surface 13 of the cartridge cover 1. The first gap 6 is formed between the first surface 211 of the staple strip body 21 and the second surface 13 of the cartridge cover 1 due to the supporting effect of the first cartridge convex portion 33. The first cartridge convex portion 33 includes a first portion and a second portion. The fist portion is located between the second surface 13 of the cartridge cover 1 and the first surface 211 of the staple strip body 21. The second portion is located between the first surface 211 of the staple strip body 21 and the upper surface of the support member 3. A height of the first portion of the first cartridge convex portion 33 is the height of the part where the first cartridge convex portion 33 protrudes from the first surface 211 of the staple strip body 21, and the height from an upper surface to a bottom surface of the first portion is equal to the height h1 of the first gap 6.

As shown in FIGS. 10 and 11, a lateral distance between an inner side and an outer side of the first cartridge convex portion 33 is smaller than that between an inner side and an outer side of the staple strip body 21, that is, a lateral width of the first cartridge convex portion 33 is smaller than that of the staple strip body 21. At least one mounting hole 212 is provided on the surface of the staple strip body 21, and the first cartridge convex portion 33 is inserted into the mounting hole 212. In this embodiment, the upper surface of the first cartridge convex portion 33 is parallel to and adheres to the second surface 13 of the cartridge cover 1, thereby enhancing cooperation stability between the first cartridge convex portion 33 and the staple strip body 21. The first cartridge convex portion 33 can be fixedly connected to the mounting hole 212 by welding, for example, to improve cooperation stability.

As shown in FIG. 11, in this embodiment, the first cartridge convex portion 33 is a boss, and a projection of the boss on the first surface 211 of the staple strip body 21 is a rounded rectangle, that is, each corner of the convex portion is provided with an arc guiding surface. When assembling the staple strip 2 with the support member 3, the arc guiding surface can better guide the boss into the mounting hole 212. The shape of the first cartridge convex portion 33 here is only an example. In other alternative embodiments, the first cartridge convex portion 33 can also be in other shapes. For example, the projection of the first cartridge convex portion 33 on the first surface 211 of the staple strip body 21 is rectangular, triangular, diamond, trapezoidal, etc. An area of an upper surface can also be different from an area of the lower surface of the first cartridge convex portion 33. For example, the convex portion 33 of the first cartridge is a vertebral structure with a larger lower surface area and a smaller upper surface area. The variations all fall within the protection scope of the present disclosure.

In this embodiment, the surface of the support member 3 is further provided with two second cartridge convex portions 34, which are respectively located on the proximal side 32 and the distal side 31 of the support member 3. A surface of the second cartridge convex portion 34 away from the support member 3 (i.e., an upper surface of the second cartridge convex portion 34) is higher than the first surface 211 of the staple strip body 21 in the height direction, the upper surface of the second cartridge convex portion 34 abuts the second surface 13 of the cartridge cover 1. The upper surface of the first cartridge convex portion 33 is at the same height as the upper surface of the second cartridge convex portion 34. In this embodiment, the lateral width of the second cartridge convex portion 34 is equal to the lateral width of the staple strip body 21. The second cartridge convex portion 34 can be fixedly connected to the staple strip body 21 by welding, for example, to improve cooperation stability between the support member 3 and the staple strip 2.

In this embodiment, the number and arrangement of the convex portions 33 of the first cartridge can be selected as needed, and can be uniformly or unevenly distributed along the axial direction on the surface of the support member 3. In another alternative implementation, the surface of the support member 3 may only be provided with the first cartridge convex portion 33, without the second cartridge convex portion 34. In another alternative embodiment, the surface of the support member 3 may only be provided with the second cartridge convex portion 34, without the first cartridge convex portion 33. In another alternative embodiment, the second cartridge convex portion 34 may be only provided on the distal side of the support member 3, or only on the proximal side of the support member 3. In another alternative implementation, the second cartridge convex portion 34 can also adopt the same shape and size as the first cartridge convex portion 33.

Figure 13:
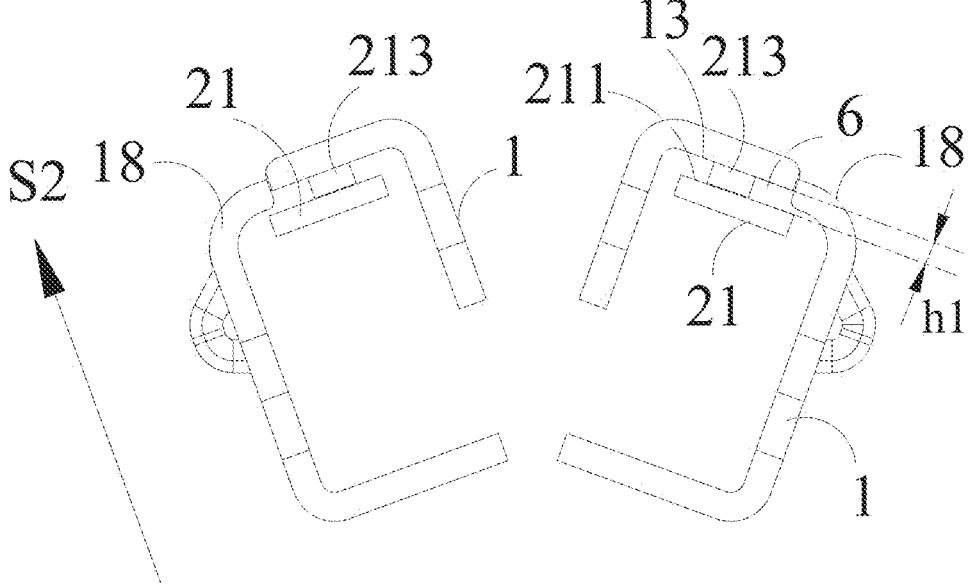
FIG. 13 is a structural schematic view of the cartridge cover cooperating with the staple strip body according to a third embodiment of the present disclosure.

FIG. 13 is a structural schematic view of the cartridge assembly according to a third embodiment of the present disclosure. In this embodiment, a third cartridge convex portion 213 is provided on the upper surface of the staple strip body 21. The upper surface of the third cartridge convex portion 213 abuts the second surface 13 of the cartridge cover 1 to form a first gap 6 between the first surface 211 of the staple strip body 21 and the second surface 13 of the cartridge cover 1. A height from an upper surface to a bottom surface of the third cartridge convex portion 213 is equal to the height h1 of the first gap 6. In this embodiment, the upper surface of the third cartridge convex portion 213 is parallel to and adheres to the second surface 13 of the cartridge cover 1 to improve cooperation stability.

The shape, size, number, and arrangement of the third cartridge convex portion 213 can be selected and set according as needed, without being limited by the embodiment shown in the drawings. By implementing this embodiment, it is also possible to achieve the purpose of conveniently driving the cutting portion 41 of the firing member 4 to separate the staple 22 from the staple strip 2.

Figure 14:
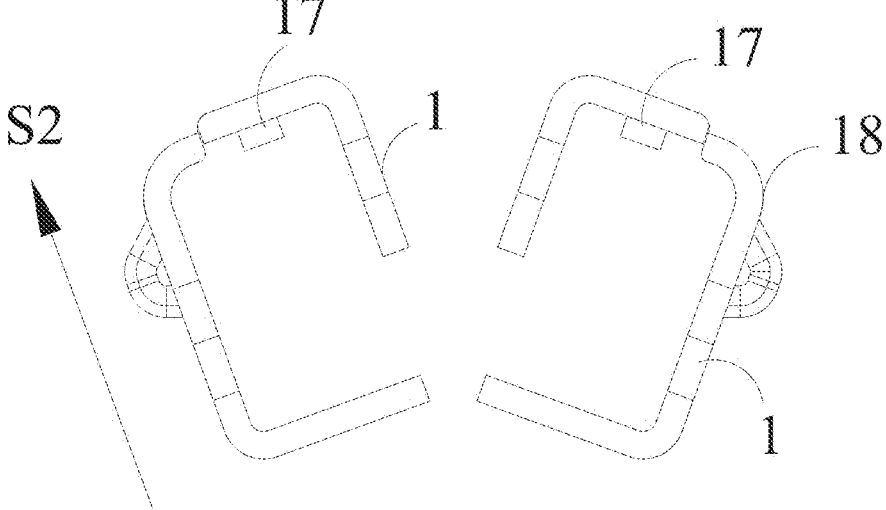
FIG. 14 is a structural schematic view of the cartridge cover according to a fourth embodiment of the present disclosure.
Figure 15:
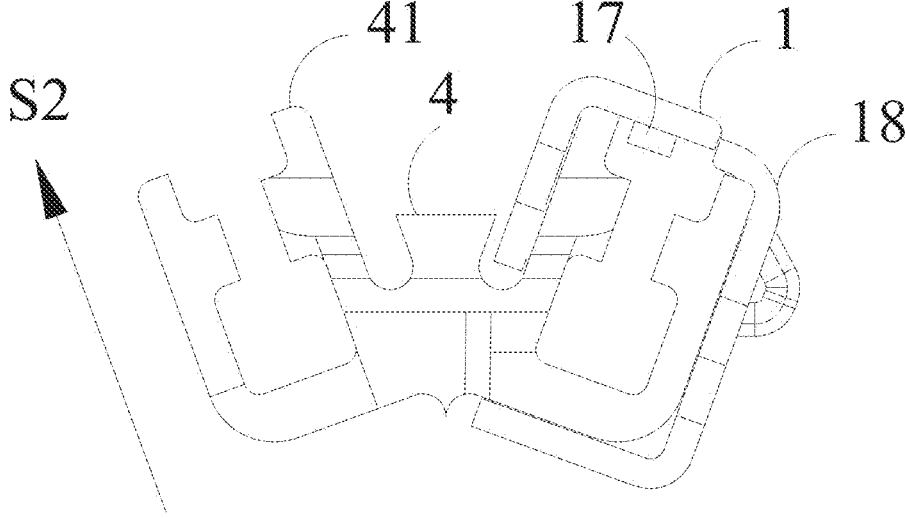
FIG. 15 is a structural schematic view of the cartridge cover cooperating with the firing member according to the fourth embodiment of the present disclosure.

FIGS. 14 and 15 are structural views of the cartridge assembly according to a fourth embodiment of the present disclosure. The difference between the fourth embodiment and the second embodiment is that in the fourth embodiment, the surface of the support member 3 is not provided with the first cartridge convex portion 33 and the second cartridge convex portion 34, while the second surface 13 of the cartridge cover 1 is provided with a fourth cartridge convex portion 17 extending towards the staple strip 2, and one surface of the fourth cartridge convex portion 17 facing the staple strip body 21 (i.e., the lower surface of the fourth cartridge convex portion 17) abuts the first surface 211 of the staple strip body 21. A height from an upper surface to a bottom surface of the fourth cartridge convex portion 17 is equal to the height h1 of the first gap 6. A lower surface of the fourth cartridge convex portion 17 is parallel to and adheres to the first surface 211 of the staple strip body 21 to improve cooperation stability. The shape, size, number, and arrangement of the fourth cartridge convex portion 17 can be selected and set as needed, without being limited by the embodiment shown in the drawings. By implementing this embodiment, it is also possible to achieve the purpose of conveniently driving the cutting portion 41 of the firing member 4 to separate the staple 22 from the staple strip 2.

The cartridge convex portions in the second embodiment, the third embodiment, and the fourth embodiment are respectively provided on the support member 3, the staple strip body 21, or the cartridge cover 1 to form the first gap 6 between the first surface 211 of the staple strip body 21 and the second surface 13 of the cartridge cover 1. In other alternative embodiments, the above three embodiments can be used in combination, for example, simultaneously setting two or more kinds of the first cartridge convex portion 33, the second cartridge convex portion 34, the third cartridge convex portion 213, and the fourth cartridge convex portion 17, all of which fall within the protection scope of the present disclosure.

Figure 16:
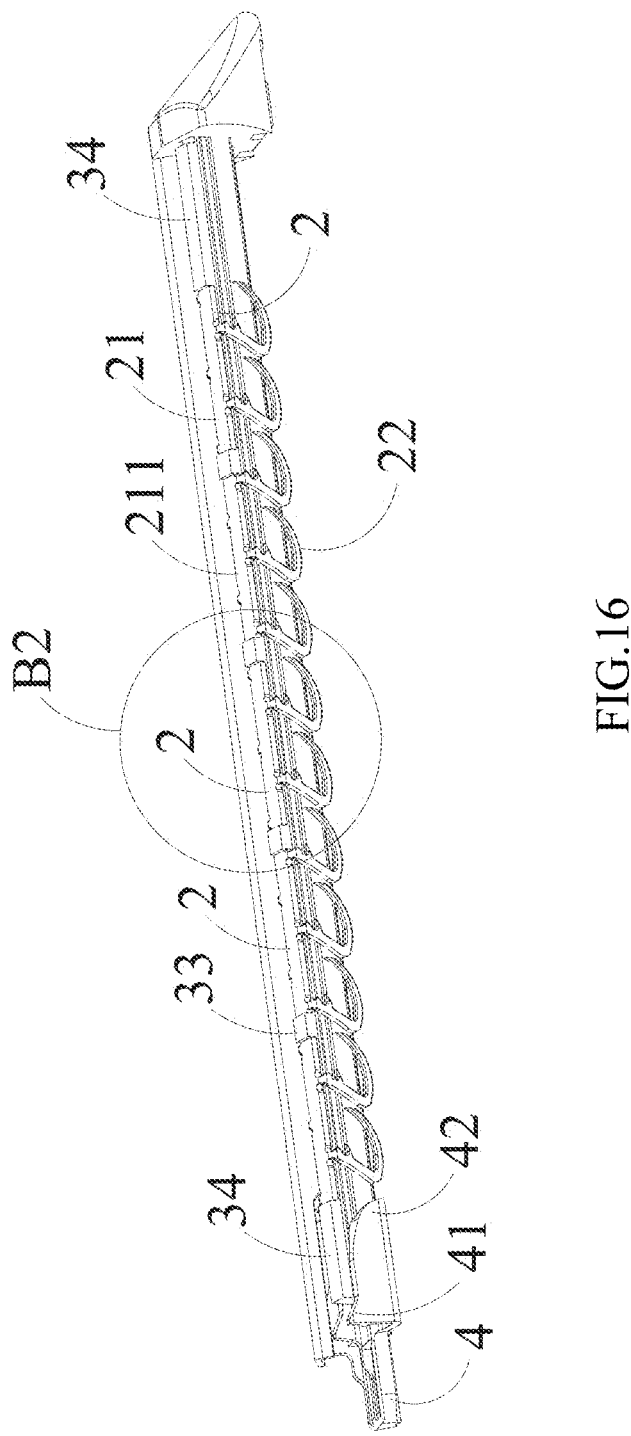
FIG. 16 is a structural schematic view of the cartridge assembly omitting the cartridge cover on one side according to a fifth embodiment of the present disclosure.
Figure 17:
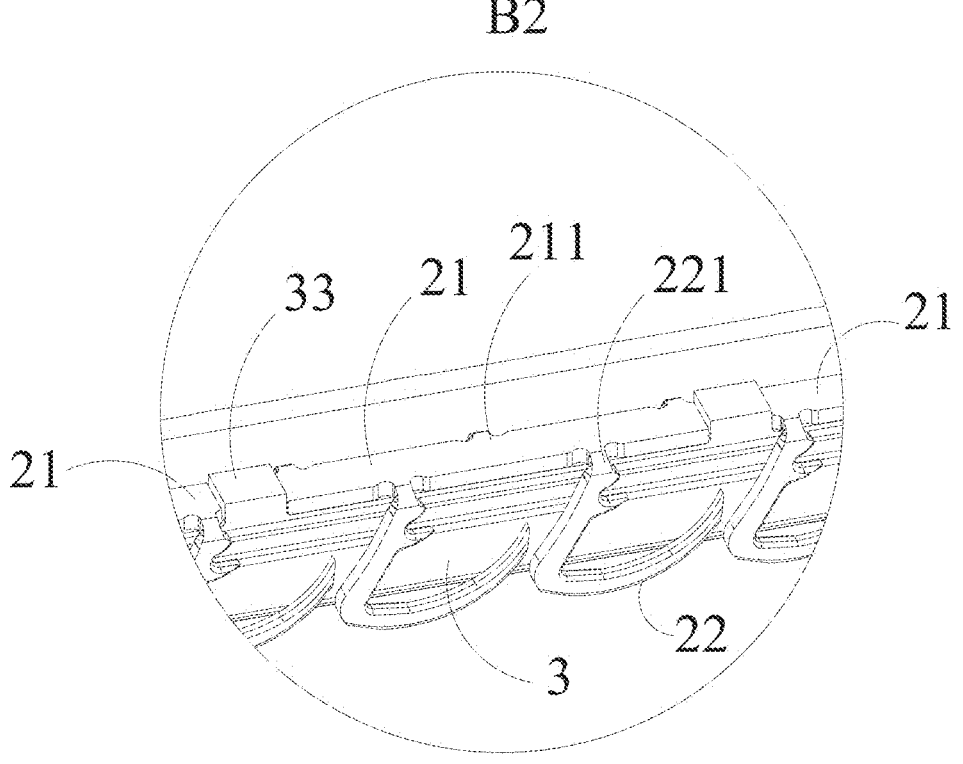
FIG. 17 is an enlarged view of B2 area in FIG. 16.

FIGS. 16 and 17 are schematic views of the combination of the staple strip and the support member in the fifth embodiment of the present disclosure. This embodiment is similar to the second embodiment in that a plurality of first cartridge convex portions 33 and two second cartridge convex portions 34 are provided on the surface of the support member 3. The two second cartridge convex portions 34 are located on the distal side 31 and the proximal side 32 of the support member 3 respectively. The first cartridge convex portions 33 are located between the two second cartridge convex portions 34, and the upper surfaces of the first cartridge convex portions 33 and the second cartridge convex portion 34 abuts the second surface 13 of the cartridge cover 1. The difference between the fifth embodiment and the second embodiment is that in the fifth embodiment, the cartridge assembly includes a plurality of staple strips 2, which are arranged along the axial direction. The first cartridge convex portion 33 is located between the staple strip bodies 21 of adjacent two staple strips 2. The two second staple convex portions 34 are located on the distal side of the most distal staple strip 2 and the proximal side of the most proximal staple strip 2 respectively. The first cartridge convex portion 33 and/or the second cartridge convex portion 34 can be fixedly connected to the staple strip 2 by welding, for example, to improve cooperation stability between the support member 3 and the staple strip 2.

As shown in FIGS. 16-17, in this embodiment, a lateral distance between an inner side and an outer side of the first cartridge convex portion 33 is equal to that of the staple strip body 21, that is, a lateral width of the first cartridge convex portion 33 is equal to that of the staple strip body 21, which can better limit the position of the staple strips 2 during installation and maintain the stability of the staple strip 2. In other alternative embodiments, the lateral distance between the inner side and the outer side of the first cartridge convex portion 33 can also be smaller than the lateral distance between the inner side and the outer side of the staple strip body 21. For example, the shape and size of the first cartridge convex portion 33 as in the second embodiment can be adopted, which also falls within the protection scope of the present disclosure.

The fifth embodiment can also have many variations, all of which fall within the protection scope of the present disclosure. The number, size, shape, and arrangement of the first cartridge convex portion 33 and the second cartridge convex portion 34 in the fifth embodiment are not limited to those shown in the drawings. The length of the staple strips 2 along the axial direction and the number of staple strips 2 are not limited to those shown in the drawings and can be adjusted as needed. In an alternative implementation, only the first cartridge convex portions 33 may be set without the second cartridge convex portion 34, or only the second cartridge convex portion 34 may be set without the first cartridge convex portions 33.

Figure 18:
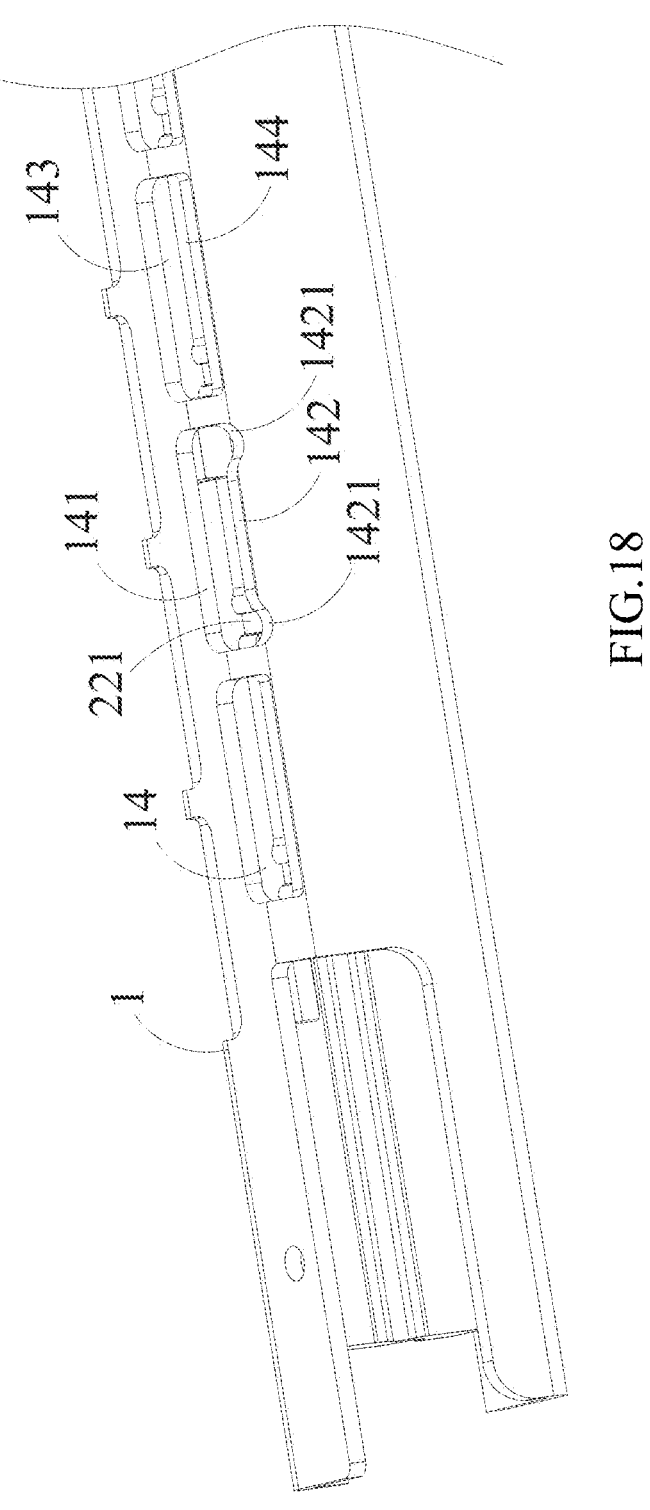
FIG. 18 is a partial structural schematic view of the cartridge assembly according to a sixth embodiment of the present disclosure.

FIG. 18 is a partial structural schematic view of the cartridge assembly according to a sixth embodiment of the present disclosure. The difference between the sixth embodiment and the first embodiment is that in the sixth embodiment, a distal end and a proximal end of the second hole wall 142 of the staple hole 14 are respectively provided with a concave arc 1421, and the lowest point of the concave arc 1421 is lower than the second hole wall 142. In FIG. 18, the second hole wall 142 of one staple hole 14 is provided with a concave arc 1421 as an example. In other embodiments, the second hole walls 142 of all the staple holes 14 may be provided with concave arcs 1421 respectively, or the second hole walls 142 of a part of the staple holes 14 may be provided with concave arcs 1421 respectively. For a staple hole 14, the concave arc 1421 can be set on both the distal end and the proximal end, or only on one of the distal and proximal ends of the second hole wall 142. By setting the concave arc 1421, the staple 22 is easier to be separated from the staple hole 14 after being formed. Selectively, in the initial state, the lowest point of the concave arc 1421 is higher than the lowest point of the connecting portion 221 of the staple 22, preventing the connecting portion 221 from completely exposing outside the staple hole 14, and improving the stability of the staple 22 in the staple hole 14 when the stapler is not fired.

Figure 19:
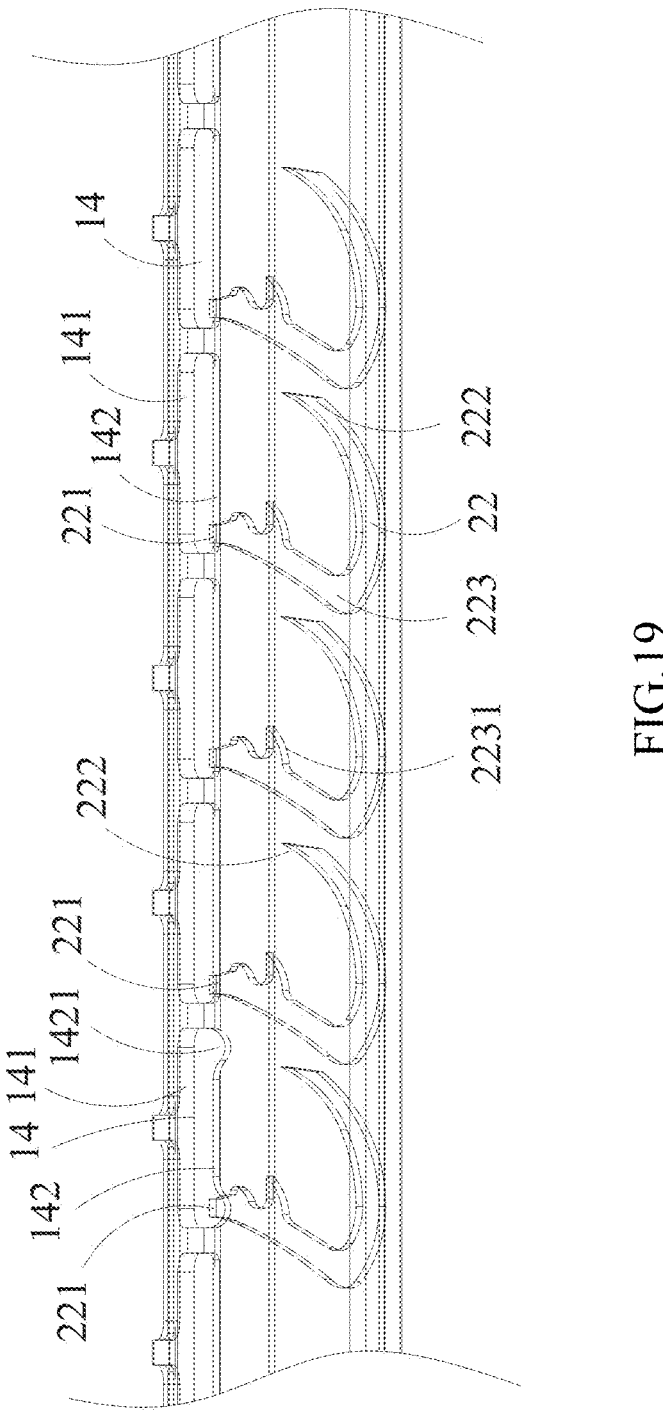
FIG. 19 and FIG. 20 schematically show staples cooperating with the cartridge cover in the embodiments.
Figure 20:
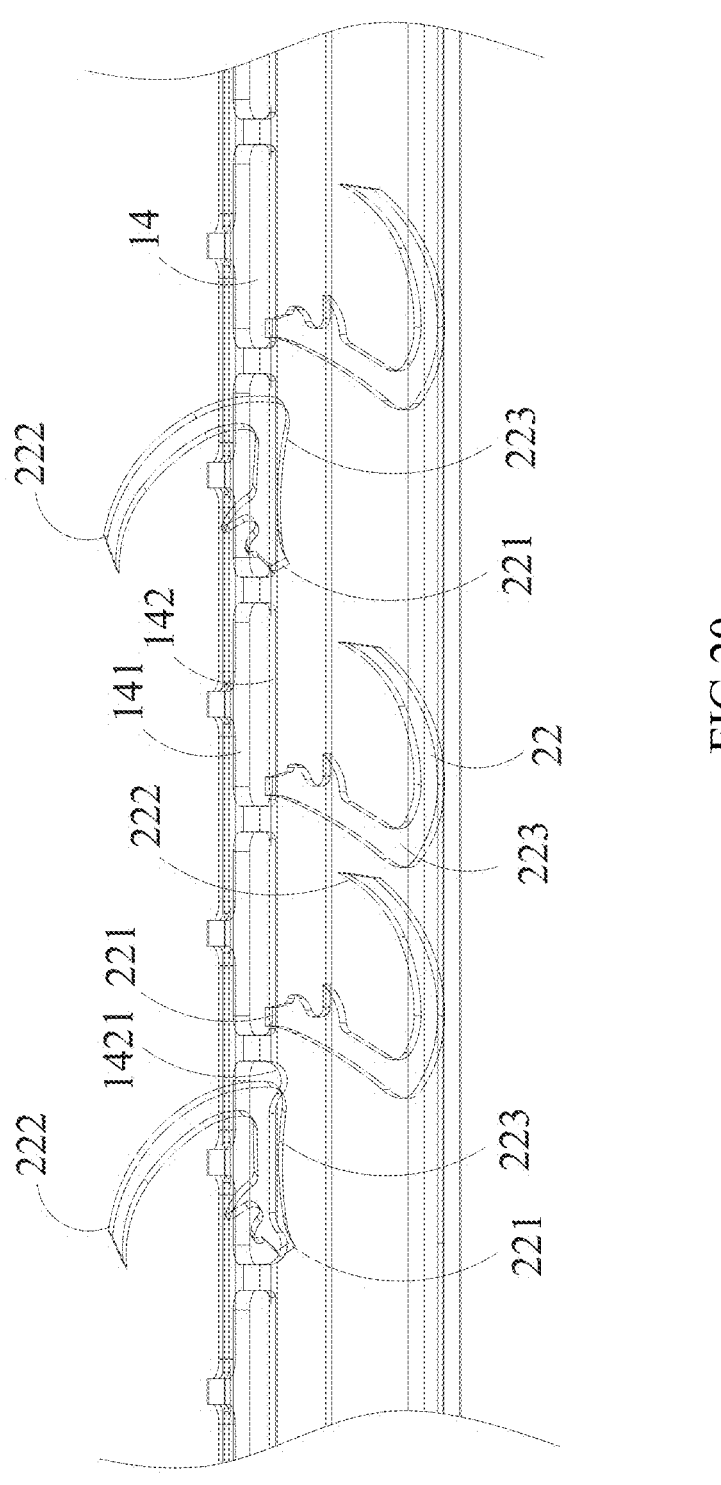

FIGS. 19 and 20 exemplify the cartridge cover cooperating with the staples. To better illustrate the cooperation between the cartridge cover 1 and the staples 22, the cartridge cover in FIGS. 19 and 20 is in a perspective form, and the support member and the staple strip body are omitted. The cooperation form between the cartridge cover and the staples in FIGS. 19 and 20 can be applied to any one of the first to sixth embodiments mentioned above, that is, it can be applied to the cooperation between the staples 22 and the cartridge cover 1 with the staple holes 14 (without concave arc 1421) in the first to fifth embodiments, or to the cooperation between the staples 22 and the cartridge cover 1 with the staple holes 14 (with concave arc 1421) in the sixth embodiment.

As shown in FIG. 19, in the initial state, the staple leg 222, the crown portion 223, and the barb 2231 of the staple 22 are all lower than the highest point of the second hole wall 142 of the staple hole 14 in the height direction. The highest point of the connecting portion 221 is higher than the highest point of the second hole wall 142 of the staple hole 14, but lower than the highest point of the first hole wall 141 of the staple hole 14. The lowest point of the connecting portion 221 is lower than the second hole wall 142 of the staple hole 14. In the embodiment with concave arc 1421, the lowest point of the connecting portion 221 is lower than the lowest point of the concave arc 1421.

When using a stapler to suture and cut tissue, the tissue between the cutting slot and the staplers on the inner side forms a lip edge, which can prevent the staples from accidentally slipping off at the edge of the tissue. However, in existing technology, after suturing and cutting tissue, a width of the lip edge is small and the function of the lip edge cannot be fully utilized.

To solve this problem, the present disclosure further provides a head assembly and a surgical stapler including the head assembly. By setting an anvil convex portion on the anvil and improving the shape of the staple hole, a wider lip edge can be obtained after tissue anastomosis, better preventing the staples from accidentally slipping off. Specifically, the head assembly includes an anvil and a cartridge assembly arranged relative to each other. The anvil surface facing the cartridge assembly is the anvil surface, and an anvil cutting slot is provided in the anvil. The anvil surface is provided with an anvil convex portion on at least one side of the anvil cutting slot, and the anvil convex portion protrudes towards the cartridge assembly. The cartridge assembly includes at least one cartridge cover, wherein a cartridge cutting slot is formed in the cartridge assembly, and a bending portion extending axially is provided on one side of the cartridge cover close to the cartridge cutting slot. The bending portion is provided with a plurality of staple holes, and the staple holes include a first hole wall and a second hole wall extending axially. The first hole wall is higher than the second hole wall in the height direction. Therefore, in the head assembly, an anvil convex portion is provided on the anvil, and the shape of the staple hole is improved. Staple holes are provided on the bending portion on one side of the cartridge cover facing the cartridge cutting slot. The second hole wall is lower than the first hole wall in the height direction, and the staple hole partially recesses in the height direction. The beneficial effect is that when the tissue is sutured and cut by the stapler, under the action of the anvil convex portion, the tissue bends downwards to form a wider lip edge compared to that in existing technology, better preventing the staples from accidentally slipping off.

Figure 21:
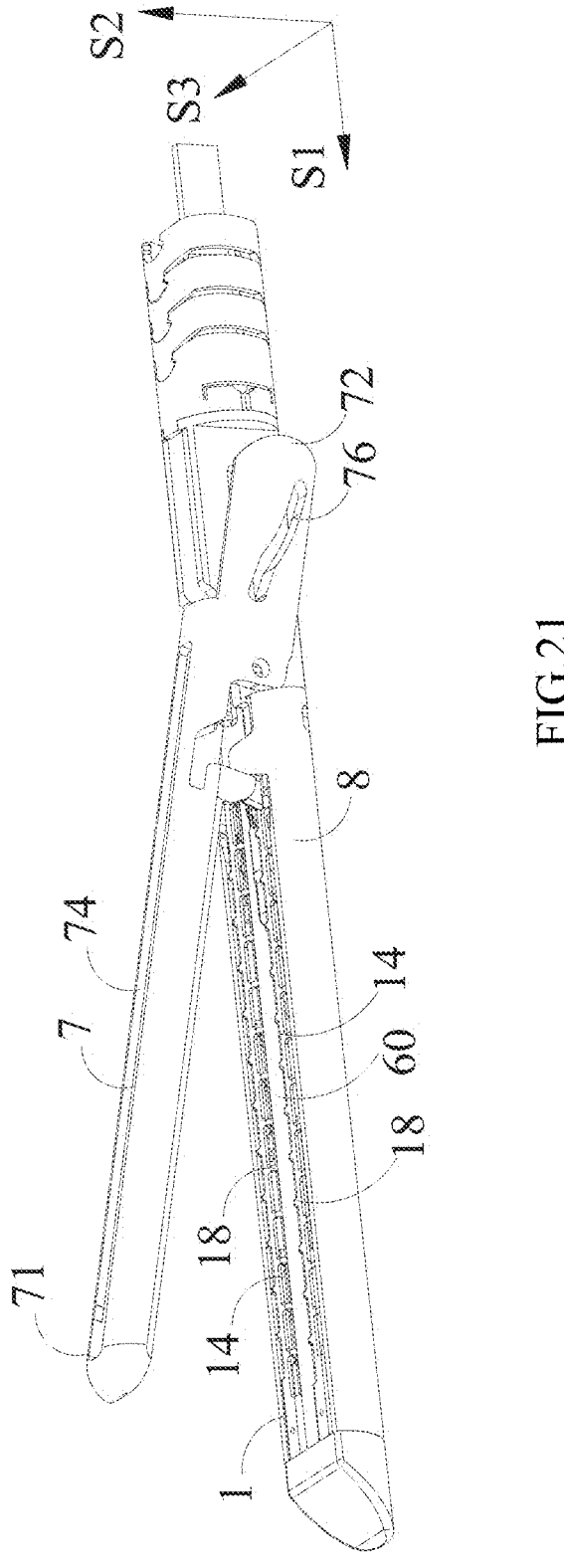
FIG. 21 is a structural schematic view of a head assembly in a first state according to a seventh embodiment of the present disclosure.
Figure 28:
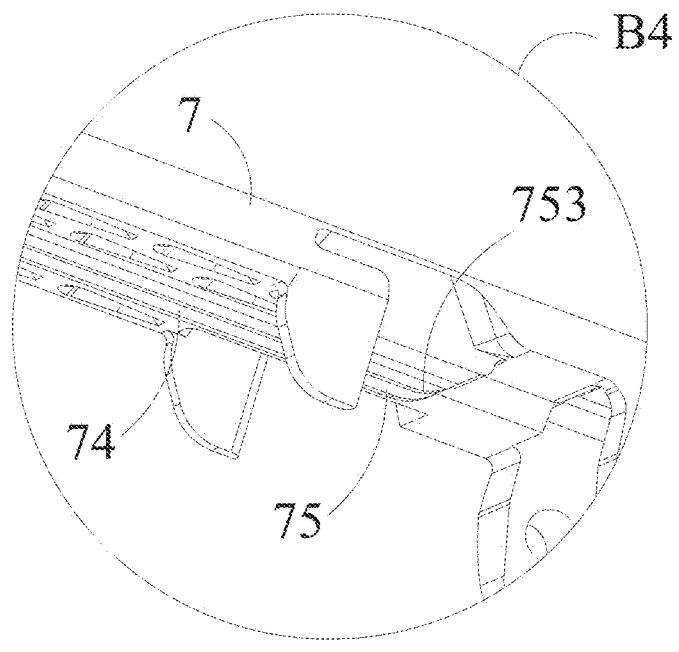
FIG. 28 is an enlarged view of B4 area of FIG. 26.
Figure 29:
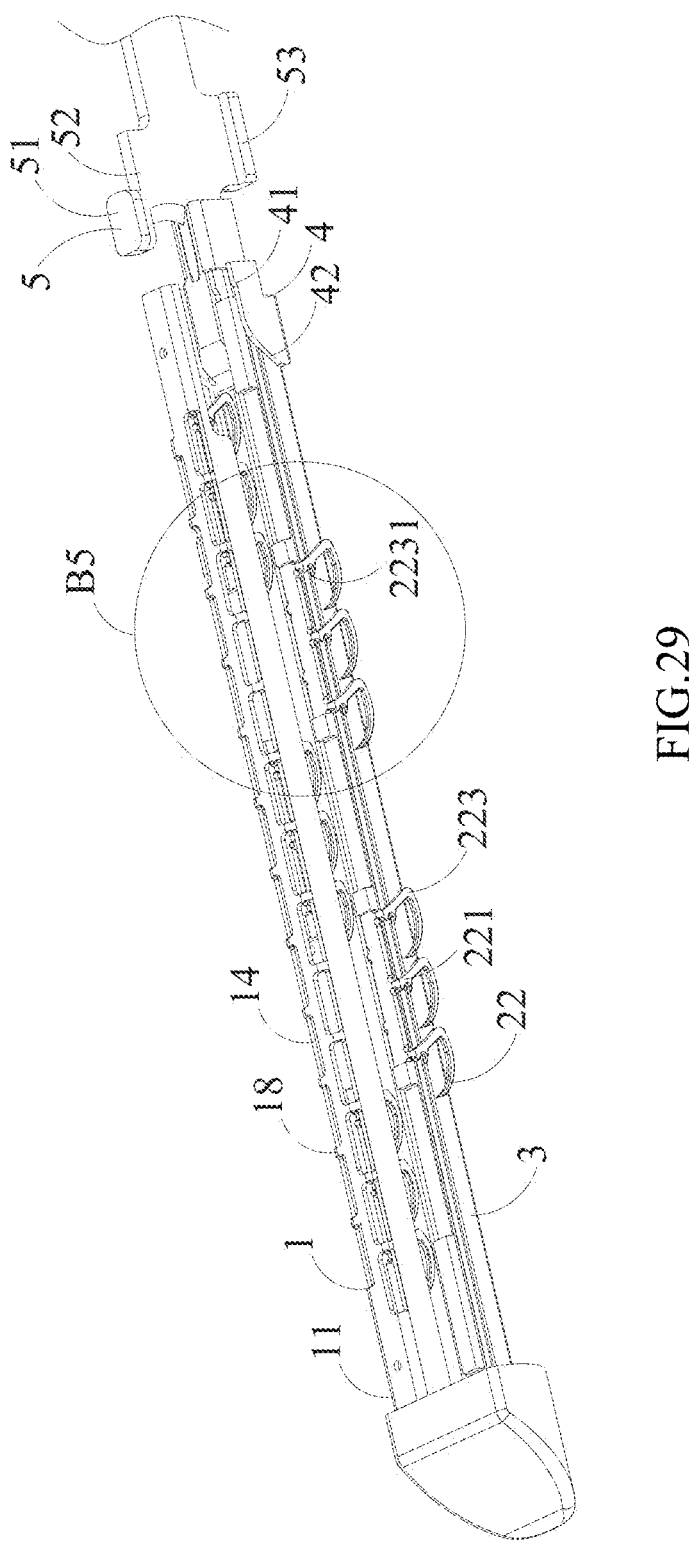
FIG. 29 is a structural schematic view of the cartridge assembly according to the seventh embodiment of the present disclosure.
Figure 30:
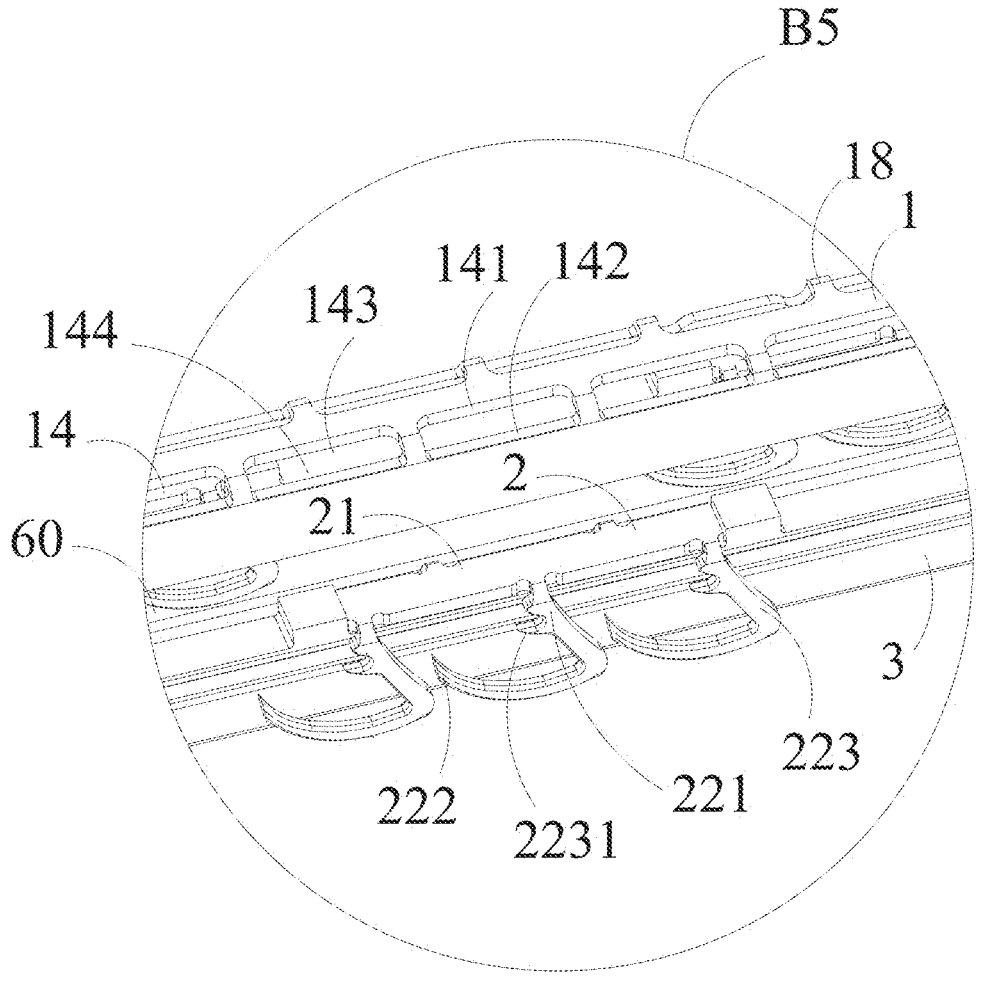
FIG. 30 is an enlarged view of B5 area of FIG. 29.
Figure 31:
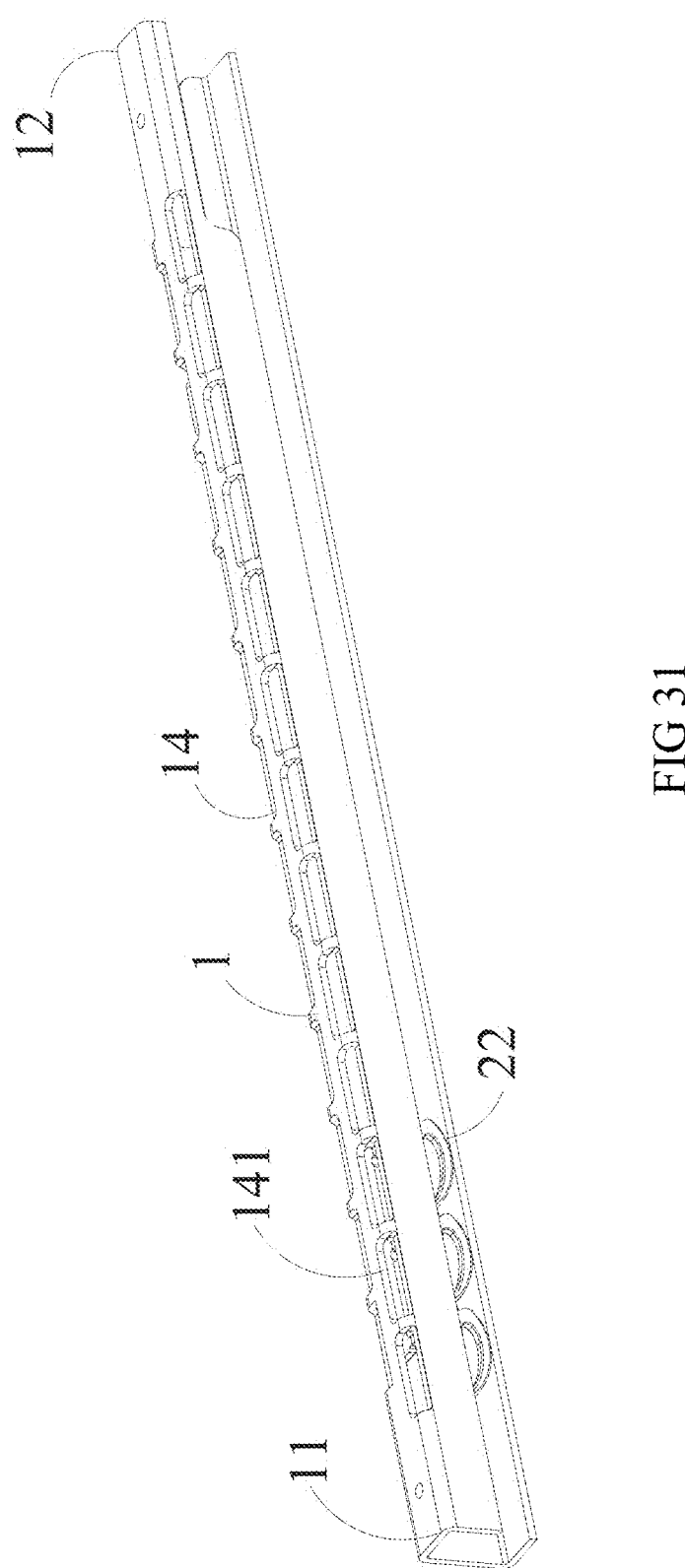
FIG. 31 is a structural schematic view of the cartridge cover cooperating with the staple strip according to the seventh embodiment of the present disclosure.

FIGS. 21-36 are structural schematic views of the head assembly according to a seventh embodiment of the present disclosure. As shown in FIGS. 21 and 22, in the seventh embodiment, the head assembly includes an anvil 7 and a cartridge assembly. The cartridge assembly includes a cartridge frame 8, a cartridge cover 1 accommodated inside the cartridge frame 8, and a staple strip 2 which is at least partially located inside the cartridge cover 1. The structure of the cartridge assembly will be introduced in detail in the following, by combining with the accompanying drawings. The head assembly has a first state and a second state. As shown in FIG. 21, when in the first state, the anvil 7 opens relative to the cartridge assembly, that is, a distal side 71 of the anvil 7 is relatively far from the cartridge assembly. As shown in FIG. 22, when in the second state, the anvil 7 is closed relative to the cartridge assembly, that is, a distal side 71 of the anvil 7 is relatively close to the cartridge assembly. A proximal side 82 of the staple frame 8 is rotatably connected to the anvil 7. Specifically, as shown in FIGS. 21 and 22, a proximal side 72 of the anvil 7 is provided with a groove 76, as shown in FIG. 25. The proximal side 82 of the staple frame 8 is provided with a long groove 83 extending axially. A connecting pin (not shown in the drawings) simultaneously passes through the groove 76 and the long groove 83, so the staple frame 8 is rotatably connected to the anvil 7. As shown in FIGS. 29 and 30, the inner space of the cartridge cover 1 accommodates a staple strip 2 and a support member 3 supporting the staple strip 2. The staple strip 2 includes a staple strip body 21 located above the support member 3 and a plurality of staples 22 at least partially located on the side of the support member 3. As shown in FIG. 29, the cutter 5 in this embodiment is an I-shaped cutter, including an upper crossbeam 51, a lower crossbeam 53, and a cutter connecting portion 52 connected between the upper crossbeam 51 and the lower crossbeam 53. An upper portion of the cutter connection portion 52 enters the anvil cutting slot 74, and a lower portion of the cutter connection portion 52 enters the cartridge cutting slot 60. When in the first state, both the cutter 5 and the firing member 4 are in the initial positions at the proximal side respectively. When the cutter pushing rod (not shown in the drawings) drives the cutter 5 from the initial position to move distally, the cutter 5 pushes the firing member 4 to move distally. At the same time, the cutter 5 drives the anvil 7 to gradually close relative to the cartridge assembly and enter the second state through the coordination of the upper crossbeam 51 and the anvil 7. At this point, if the cutter pushing rod continues to push the cutter 5 distally, the cutter 5 will continue to push the firing member 4 distally. The firing member 4 will push the staples 22 to suture tissue, while the cutter 5 cuts the tissue to complete the process of firing the stapler.

Figure 23:
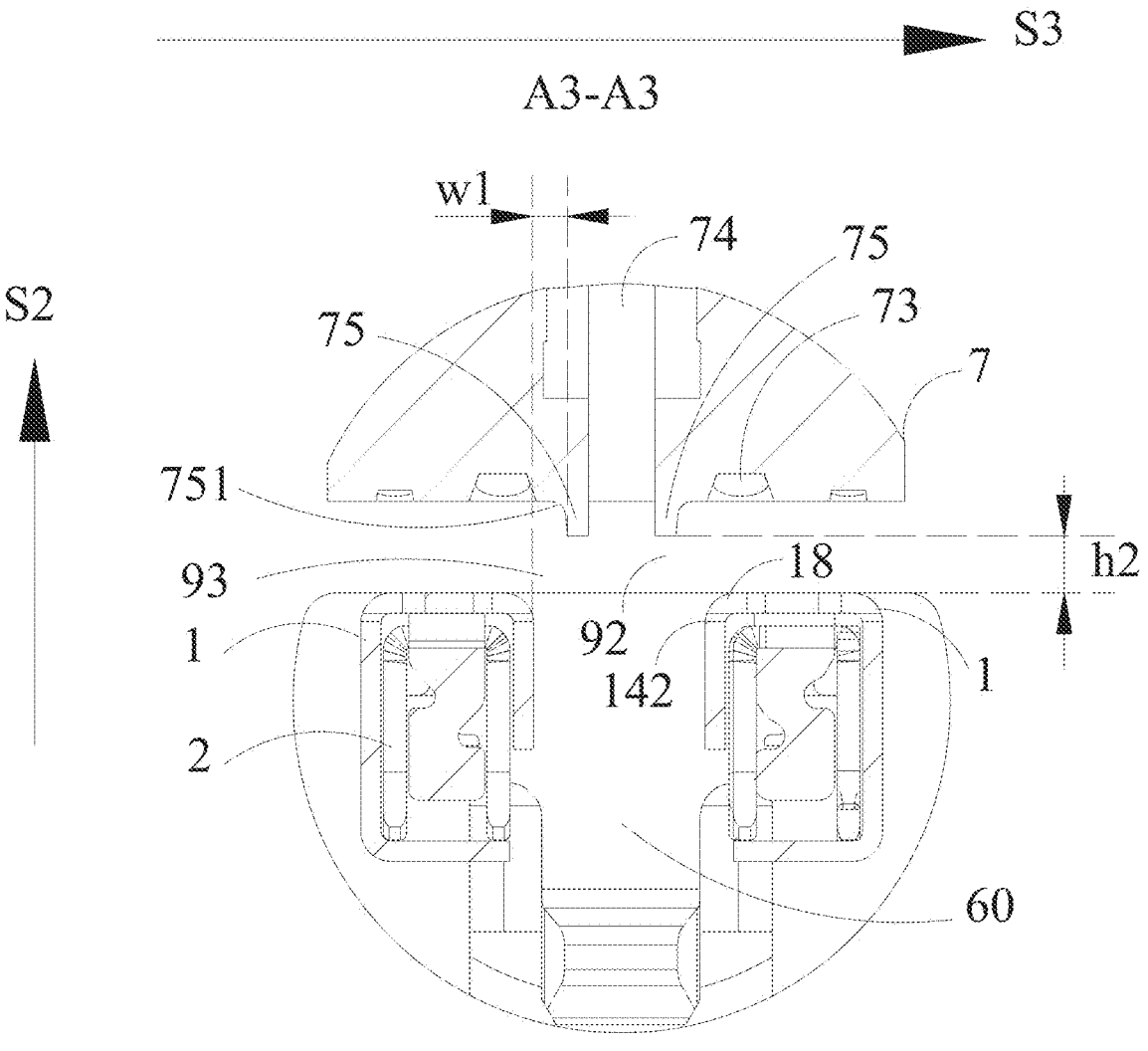
FIG. 23 is a cross-sectional view of A3-A3 Direction of FIG. 22.
Figure 26:
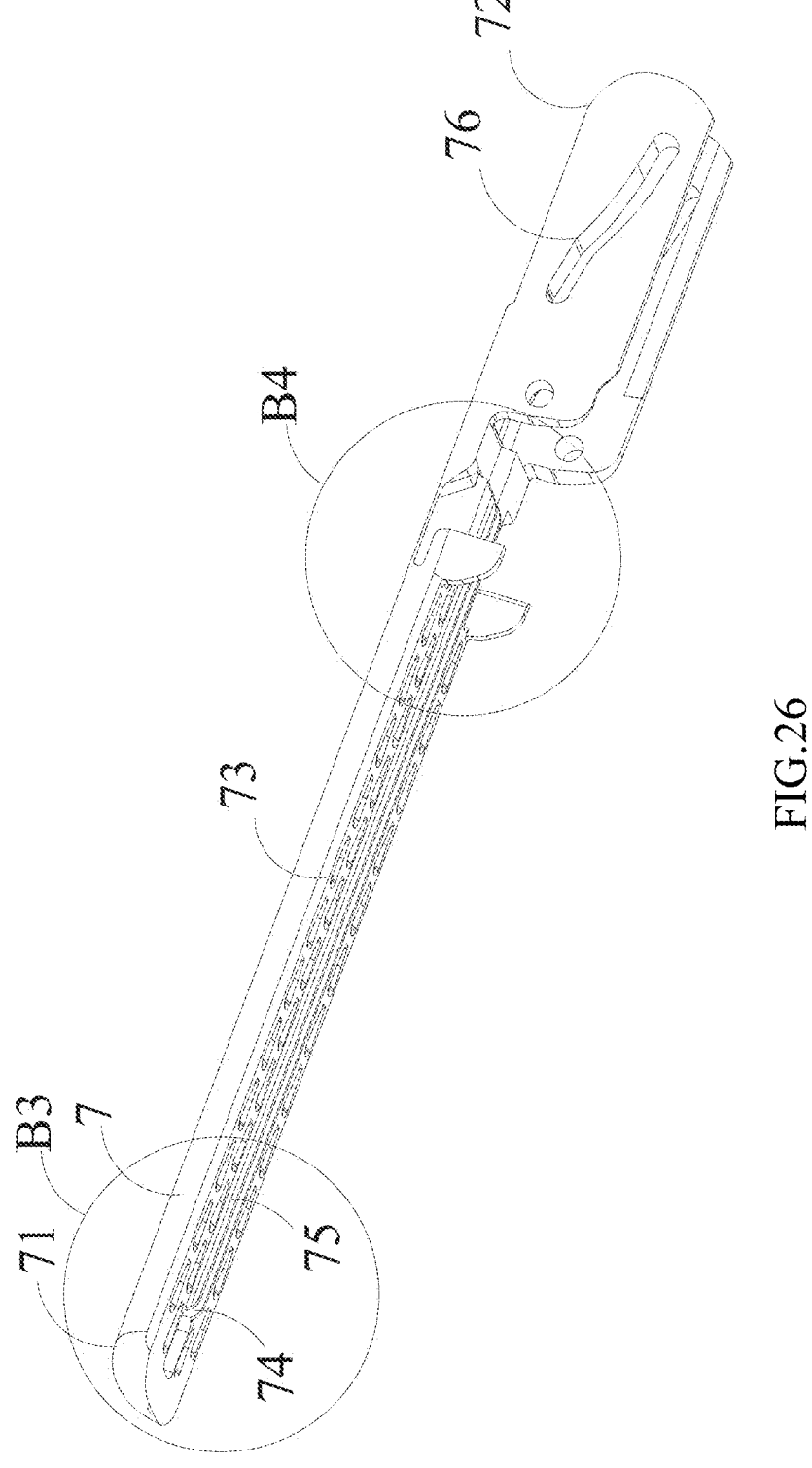
FIG. 26 is a structural schematic view of an anvil according to the seventh embodiment of the present disclosure.
Figure 27:
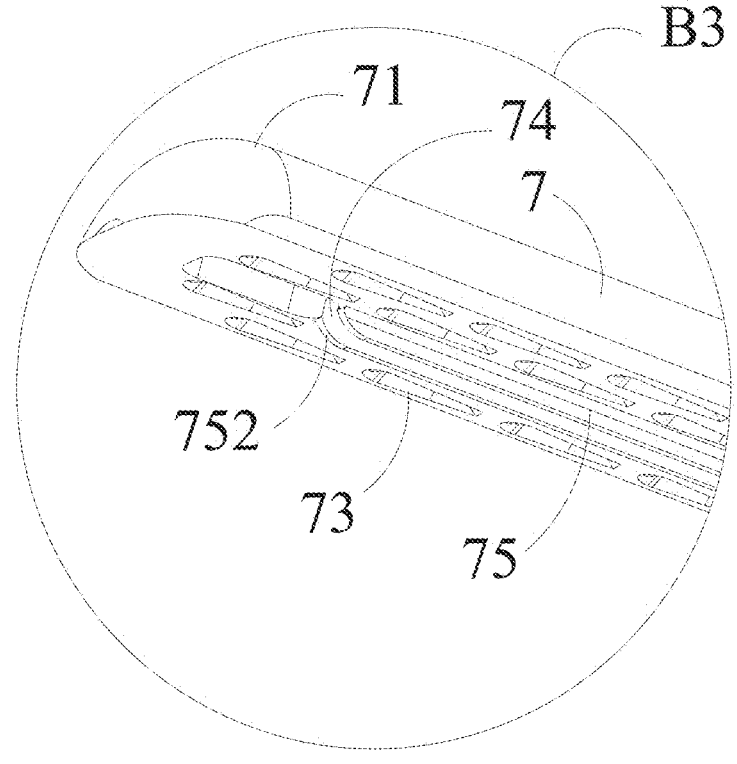
FIG. 27 is an enlarged view of B3 area of FIG. 26.

As shown in FIGS. 23 and 26, the side of the anvil 7 facing the cartridge assembly is the anvil surface (i.e., in the perspective of FIG. 23, the lower surface of the anvil 7), and the anvil surface is provided with a plurality of anvil holes 73. The positions of the anvil holes 73 correspond to the staples 22 in the cartridge assembly. The anvil 7 is provided with an anvil cutting slot 74, and the anvil surface is provided with an anvil convex portion 75 on at least one side of the anvil cutting slot 74. The anvil convex portion 75 extends towards the cartridge assembly. In this embodiment, the anvil surface is provided with anvil convex portions 75 on both sides of the anvil cutting slot 74, and the anvil convex portions 75 include a convex bar extending along the axial direction of the stapler. The convex bar can be integrally formed with the anvil 7, or the convex bar and the anvil 7 can also be two separately formed parts, which are fixed and connected to each other through welding or other methods. In other embodiments, the anvil convex portion 75 may include a plurality of bulges arranged along the axial direction. As shown in FIG. 23, an arc surface 751 which is concave inward is provided on the outer side of the anvil convex portion at the connecting position with the anvil surface. When the anvil 7 is closed relative to the cartridge assembly and clamps the tissue, the surface of the outer side of the anvil convex portion 75 contacting the tissue is a circular arc surface 751 instead of a right angle surface, to avoid damage to the tissue. As shown in FIGS. 26-28, in this embodiment, a distal surface of the anvil convex portion 75 is a first guiding surface 752, and a proximal side of the first guiding surface 752 inclines proximally compared to the distal side. Selectively, the transition between the first guiding surface 752 and a lower surface of the anvil convex portion 75 is smooth. The proximal surface of the anvil convex portion 75 is a second guiding surface 753, and the distal side of the second guiding surface 753 inclines distally compared to the proximal side. Selectively, the transition between the second guiding surface 753 and the lower surface of the anvil convex portion 75 is smooth. By providing the first guide surface 752 and the second guide surface 753, as the anvil 7 gradually closes from the open state, the anvil convex portion 75 can better fit with the tissue and better accommodate the tissue between the anvil 7 and the cartridge assembly.

Figure 24:
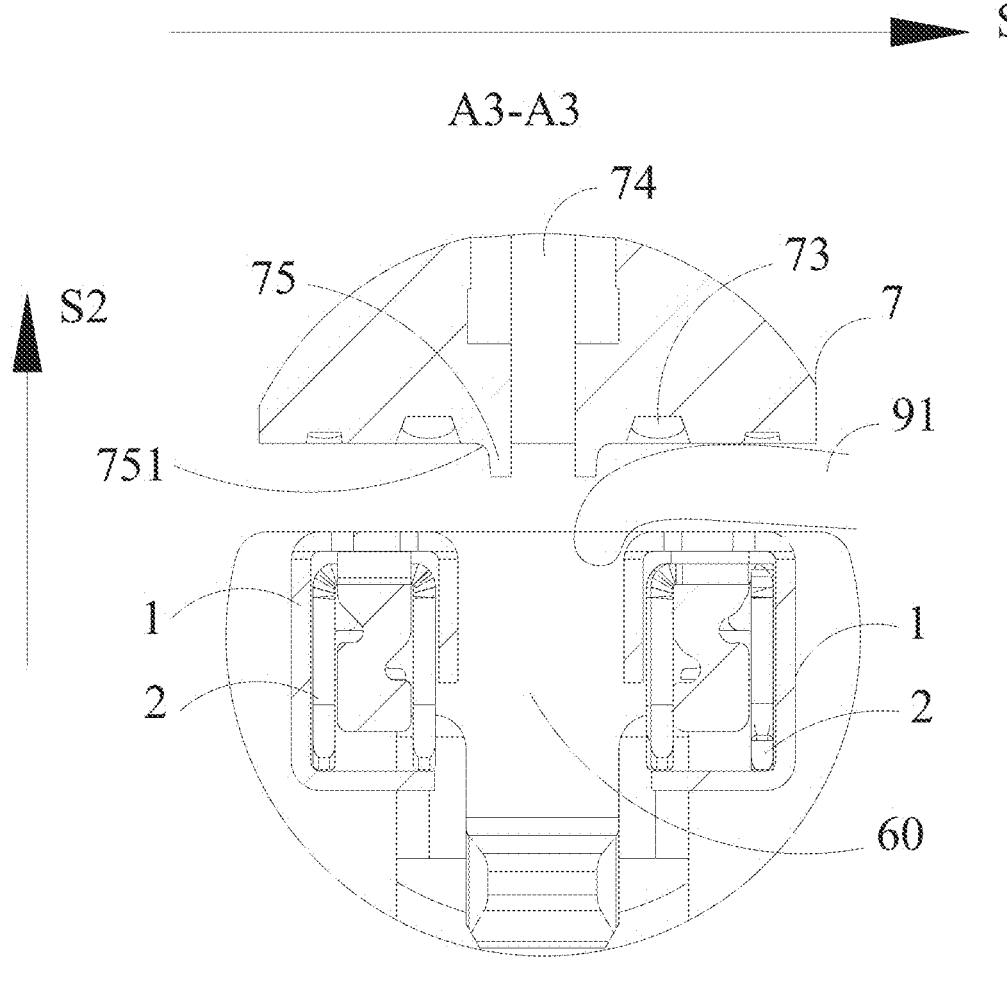
FIG. 24 is a schematic view of suturing tissue according to the seventh embodiment of the present disclosure.
Figure 32:
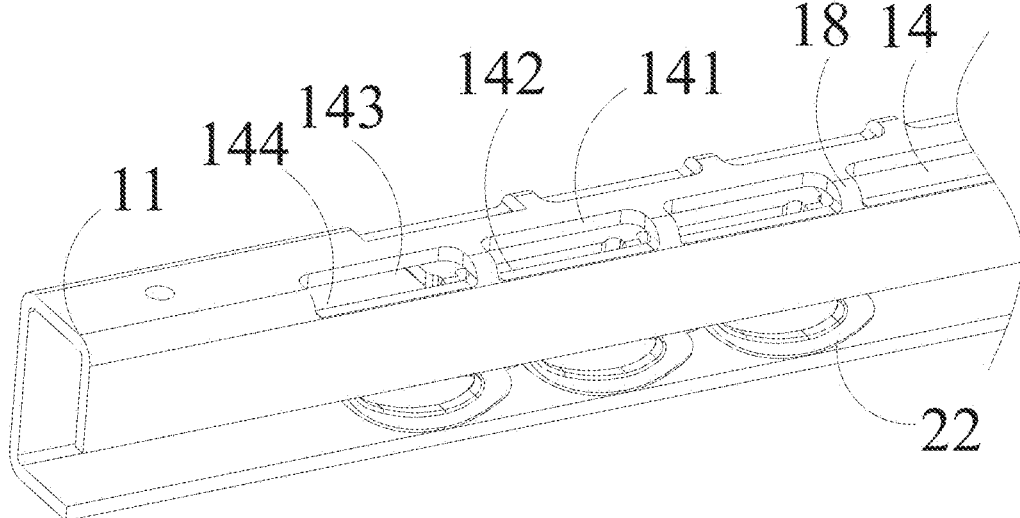
FIG. 32 is a partial structural schematic view of the cartridge cover cooperating with the staple strip according to the seventh embodiment of the present disclosure.

As shown in FIGS. 29 and 32, a cartridge cutting slot 60 is formed in the cartridge assembly. On both sides of the cartridge cutting slot 60 of the cartridge assembly, there are two cartridge covers 1, which are symmetrically arranged relative to the cartridge cutting slot 60. The staple strip 2 set in each cartridge cover 1 can be a long strip extending along the axial direction, or includes a plurality of staple strips 2 arranged in sequence along the axial direction. In this embodiment, two rows of staples 22 are respectively arranged on two sides of the staple strip body 21, and the two rows of staples 22 are arranged in a staggered manner along the axial direction. In other alternative embodiments, the staples 22 can be only set on one side of the staple strip body 21. A bending portion 18 extending along the axial direction is provided on one side of the cartridge cover 1 (inner side of the cartridge cover 1) close to the cartridge cutting slot 60, and the bending portion 18 has a smooth surface. The bending portion 18 is provided with a plurality of staple holes 14, each staple hole includes a first hole wall 141 and a second hole wall 142 extending along the axial direction. The first hole wall 141 is higher than the second hole wall 142, that is, the second hole wall 142 recesses in the height direction relative to the first hole wall 141 and extends to the side plate of the cartridge cover 1. The first hole wall 141 and the second hole wall 142 are located on different planes. Specifically, the first hole wall 141 is located on the upper plate of the cartridge cover 1, and the second hole wall 142 is located on the side plate of the cartridge cover 1. FIGS. 23, 24, and 29 show that by setting a convex portion 75 on the anvil 7 and improving the shape of the staple hole 14, the staple holes 14 are set at the bending portion 18 on the side of the cartridge cover 1 facing the cartridge cutting slot 60. The second hole wall 142 is lower than the first hole wall 141, and the staple hole 14 partially recesses in the height direction, so that when the stapler sutures and cuts tissue 91, more tissue 91 can enter into the open space of the staple holes 14, and bends downwards to form a wider lip edge compared to that of the existing technology, better preventing the staple 22 from accidentally slipping off.

As shown in FIG. 23, in this embodiment, when in the second state, a second gap 92 in the height direction (S2 direction) is formed between the lowest point of the anvil convex portion 75 and the upper surface of the cartridge cover 1, and a height from an upper side to a bottom side of the second gap 92 is h2. A third gap 93 in the width direction (S3 direction) is formed between an outer wall of the anvil convex portion 75 and an inner wall of the cartridge cover 1 (the side wall of the cartridge cover 1 close to the side of the cartridge cutting slot 60), and the width of the third gap 93 is w1. By forming the second gap 92 and the third gap 93, enough space is formed to accommodate the tissue when the head assembly clamps the tissue between the anvil 7 and the cartridge assembly, so that the tissue can bend towards the cartridge cutting slot 60, thereby increasing the width of the lip edge.

As shown in FIGS. 29 and 30, the staple 22 includes a connecting portion 221, which is rotatably connected to the staple strip body 21 via the connecting portion 221. Since the first hole wall 141 and the second hole wall 142 are not on the same plane, the formed staple hole 14 is a three-dimensional staple hole 14, so a larger exposing space is formed on the cartridge cover 1, that is, the staple hole 14 is recessed downwards and extends to the side plate of the cartridge cover 1. In this way, when closed, the tissue can fully enter the contour of the staple 22, and the staple 22 can better puncture the tissue and achieve anastomosis. At the same time, the staple 22 is easier to pass upwards through the staple hole 14 and be separated from the cartridge cover 1 after being closed.

As shown in FIG. 29, the firing member 4 includes a staple pushing portion 42 and a cutting portion 41. During the process of firing the stapler, the firing member 4 moves from the proximal side of the cartridge assembly to the distal side of the cartridge assembly. The staple pushing portion 42 of the firing member 4 first contacts the crown portion 223 of the staple 22, drives the staple leg 222 of the staple 22 to rotate around the connecting portion 221, and extends upwards from the staple hole 14, then the staple 22 is closed into a D-shape under the action of the anvil 7. The cutting portion 41 cuts the connecting portion 221, and the staple 22 can be separated from the staple strip body 21, move upwards through the staple hole 14 and be closed on the tissue, then the staple 22 can be separated from the cartridge cover 1. As shown in FIGS. 29 and 30, during the process of rotating the staple 22, at least a part of the side wall of the staple 22 simultaneously abuts the inner wall of the side plate of the support member 3 and the cartridge cover 1, so that the position of the side wall of the staple 22 is always limited, preventing the staple 22 from shifting inward or outward during the process of rotating the staple 22.

As shown in FIGS. 29 and 30, the cartridge cover 1 includes two bending portions 18 located on both sides of the staple strip 2 respectively. One bending portion 18 is connected to the upper plate and the left plate of the cartridge cover 1, and the other bending portion 18 is connected to the upper plate and the right plate of the cartridge cover 1. The surface of the bending portion 18 is a smooth circular arc surface. The staple holes 14 of the bending portions 18 on both sides of the staple strip 2 are three-dimensional staple holes 14 with two hole walls that are not on the same plane. The staple holes 14 on both sides of the staple strip 2 are in recessed form, allowing more tissue to enter the openings of the staple holes 14 on both sides of the cartridge cover 1, making the staples 22 easier to puncture tissue and be formed. At the same time, the staple holes 14 partially recess in the height direction, making the staples 22 easier to be separated from the cartridge cover 1 after being closed, improving the surgical effect. In another alternative implementation, three-dimensional staple holes 14 with two hole walls that are not in the same plane can be set only on the inner side of the cartridge cover 1 (the side near the cartridge cutting slot 60) at the bending portion 18, while the staple holes set on the outer side of the cartridge cover 1 (away from the side of the cartridge cutting slot 60) are in the same plane, that is, another type of staple holes are set on the outer side of the upper plate of the cartridge cover 1, the first and second hole walls of this other type of staple hole are both located on the upper plate of the cartridge cover 1.

Figure 33:
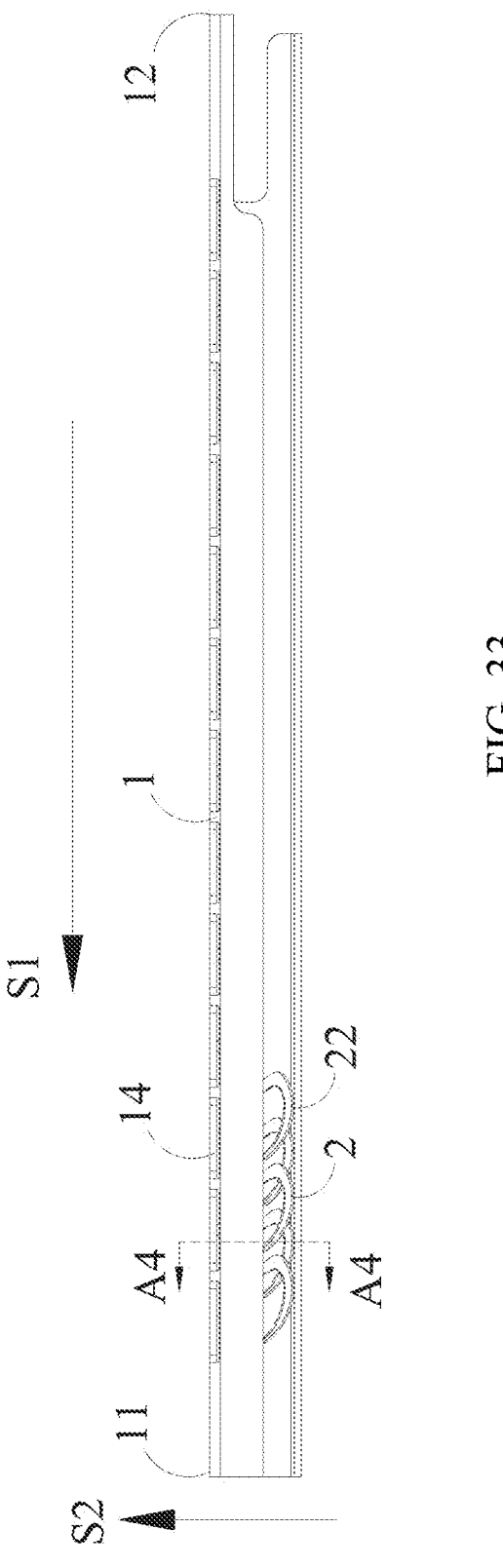
FIG. 33 is a front view of the cartridge cover cooperating with the staple strip according to the seventh embodiment of the present disclosure.
Figure 35:
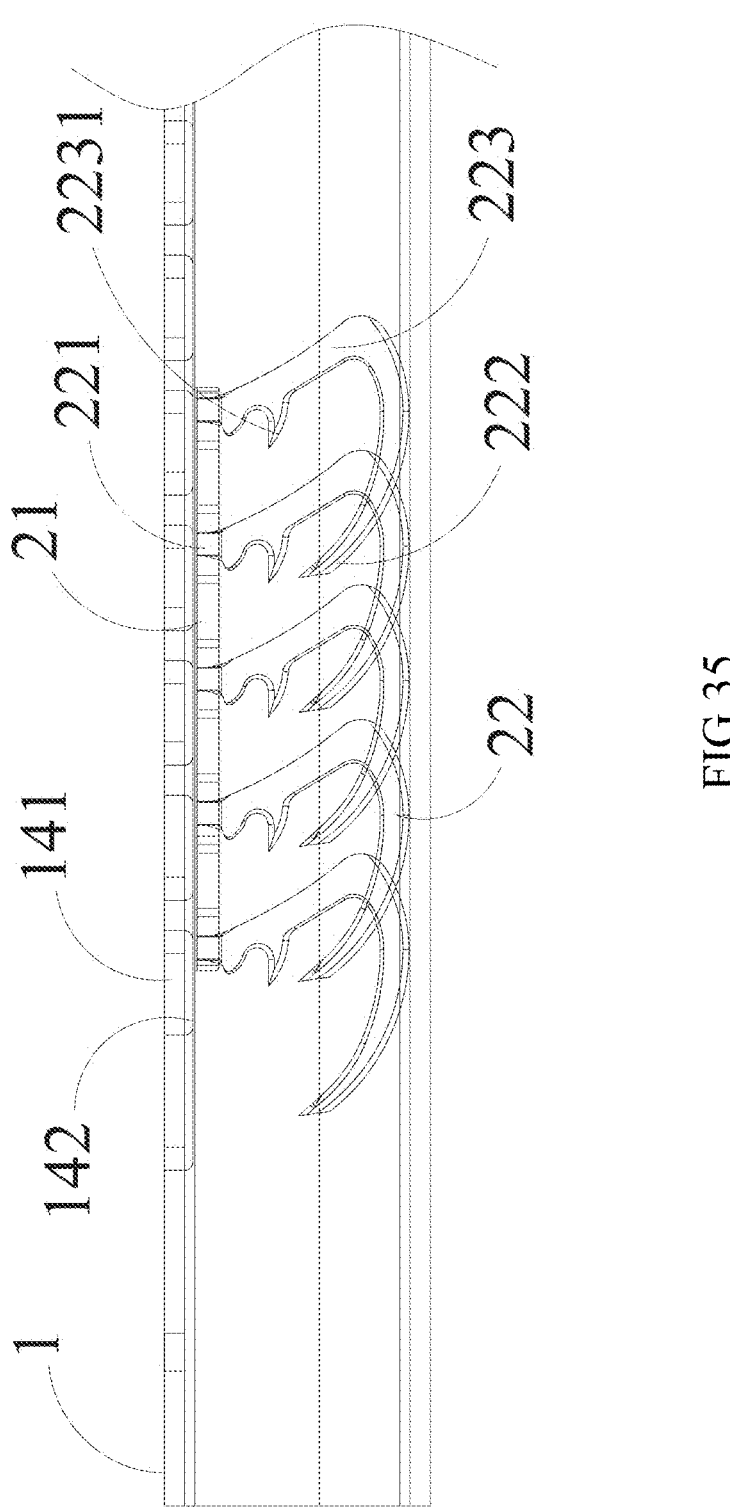
FIG. 35 is a partial structural schematic view of the cartridge cover cooperating with the staple strip according to the seventh embodiment of the present disclosure.

As shown in FIGS. 29 and 30, in this embodiment, the bending portion 18 is connected between the upper plate and one side plate of the cartridge cover 1. The staple hole 14 includes a first section 143 and a second section 144 connected to each other. The first section 143 of the staple hole 14 is located on the upper plate of the cartridge cover 1, and the second section 144 of the staple hole 14 is located on the side plate of the cartridge cover 1, The first section 143 of the staple hole 14 has the first hole wall 141 on the side away from the second section 144, and the second section 144 of the staple hole 14 has the second hole wall 142 on the side away from the first section 143. In this embodiment, the first hole wall 141 is parallel to a surface of the side plate of the cartridge cover 1, and the second hole wall 142 is parallel to a surface of the upper plate of the cartridge cover 1. In this embodiment, the highest point of the connecting portion 221 of the staple 22 is lower than the highest point of the first hole wall 141 of the staple hole 14 in the height direction. The highest point of the connecting portion 221 will not protrude from the upper plate of the cartridge cover 1. Therefore, when the stapler is not fired, the connecting portion 221 will not contact with the tissue. The lowest point of the connecting portion 221 of the staple 22 is lower than the highest point of the second hole wall 142 of the staple hole 14 in the height direction, so that in the initial state, the connecting portion 221 will not be completely exposed outside the staple hole 14, so that the stability of the staple 22 in the staple hole 14 is improved when the stapler is not fired. As shown in FIGS. 33 and 35, in this embodiment, the highest point of the connecting portion 221 is lower than the second hole wall 142 in the height direction. In another alternative implementation, the highest point of the connecting portion 221 can also be higher than the second hole wall 142 and lower than the first hole wall 141, so that the connecting portion 221 is partially exposed outside the staple hole 14, but not completely exposed, so that the staple 22 is easier to be separated from the staple hole 14 after the staple 22 rotates and be closed.

Figure 34:
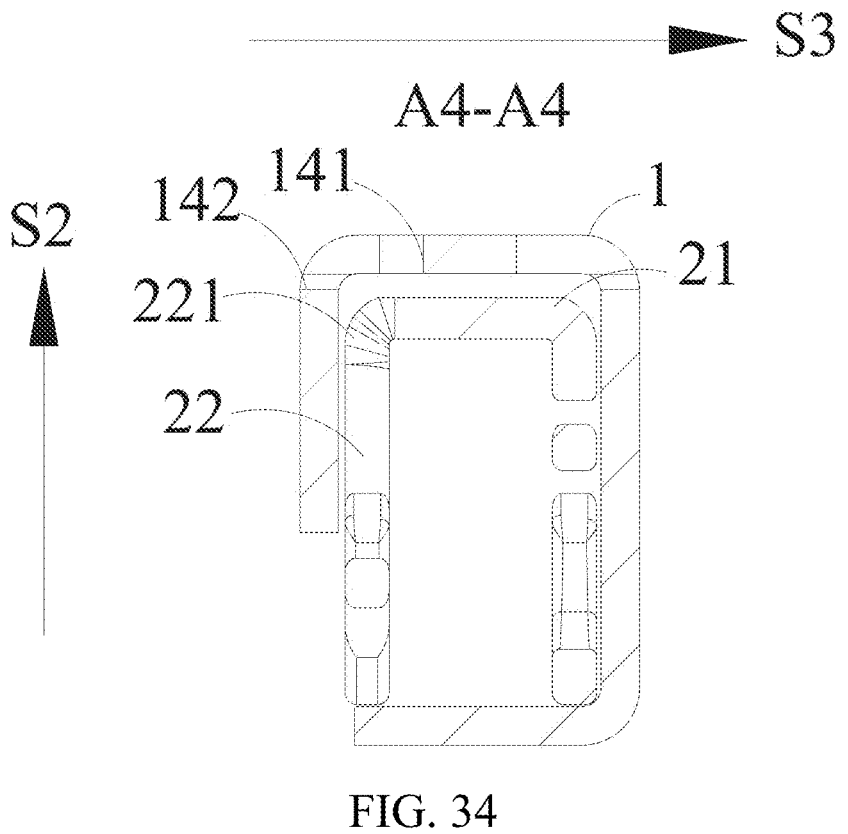
FIG. 34 is a cross-sectional view of A4-A4 direction of FIG. 33.

As shown in FIGS. 32 and 34, the distance between the first hole wall 141 and the second hole wall 142 of the staple hole 14 in the lateral direction (S3 direction) is greater than the distance between the two sides of the staple 22 in the lateral direction (S3 direction), that is, the width of the staple hole 14 is greater than the width of the staple 22, so that the staple 22 can completely pass through the staple hole 14 without being stuck when the stapler is fired. In this embodiment, the projection of the staple 22 on the upper plate of the cartridge cover 1 falls within the coverage range of the projection of the staple hole 14 on the upper plate of the cartridge cover 1. When the firing member 4 drives the staple 22 to move upwards, the staple 22 can pass through the staple hole 14 more smoothly without being obstructed by the wall of the staple hole 14 or getting stuck inside the staple hole 14.

Figure 36:
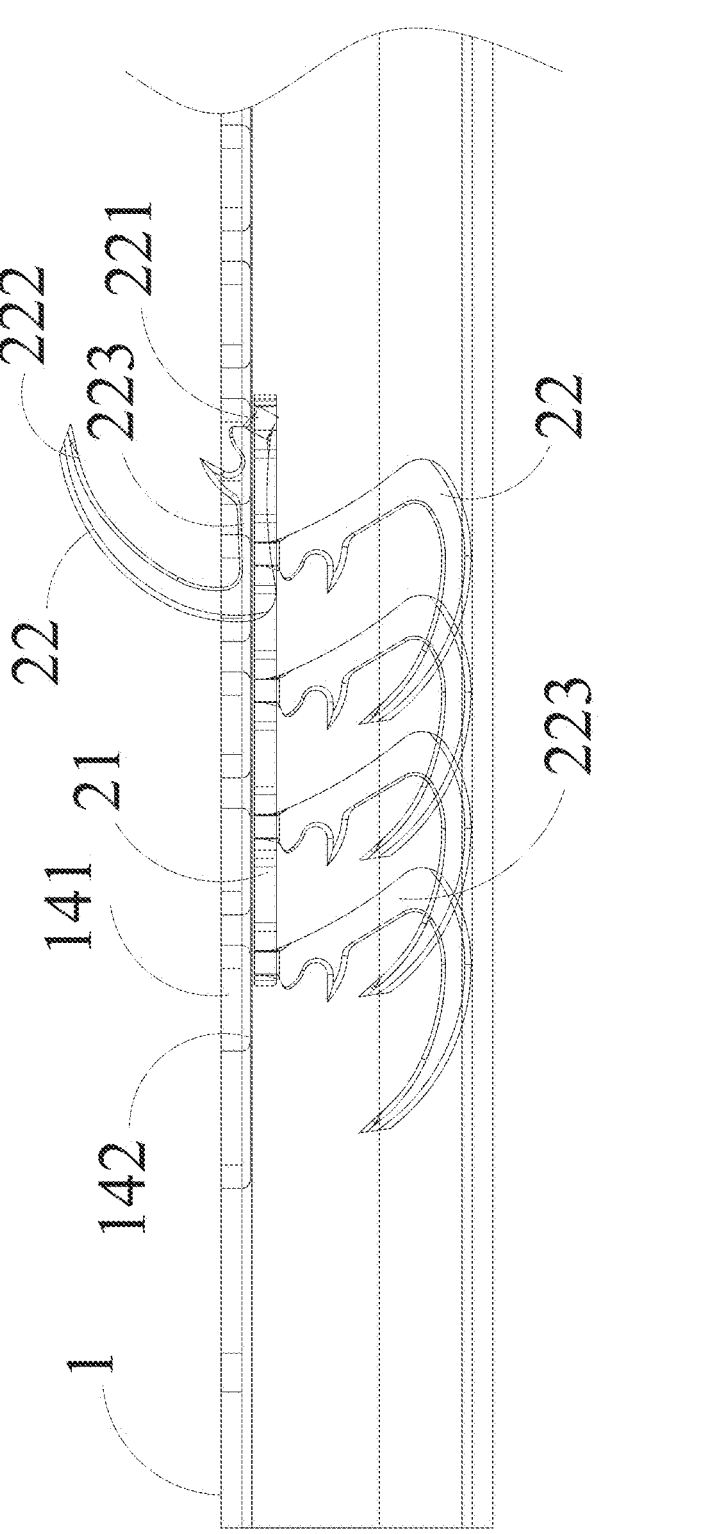
FIG. 36 is a partial structural schematic view of the cartridge cover cooperating with the staple strip and one staple being closed according to the seventh embodiment of the present disclosure.

As shown in FIGS. 35 and 36, the staple 22 further comprises a crown portion 223 and a staple leg 222. The crown portion 223 is connected to the connecting portion 221, and the side of the crown portion 223 facing the distal side is provided with a barb 2231. In FIGS. 35 and 36, in order to better illustrate the relationship between the cartridge cover 1 and the staple strip 2, the cartridge cover 1 is shown in perspective form, only showing its constituent lines. As shown in FIG. 35, in the initial state, the second hole wall 142 is set higher than the barb 2231 to avoid exposing the barb 2231 outside the staple hole 14 and scratching the tissue. The highest point of the staple leg 222 is also lower than the second hole wall 142 in the height direction to avoid exposing the staple leg 222 outside the staple hole 14 and scratching the tissue in the initial state.

In the above embodiment, the anvil convex portion 75 set on the anvil surface includes a convex portion extending along the axial direction of the stapler. In another alternative embodiment, the anvil convex portion 75 may include a plurality of convex portions arranged along the axial direction of the stapler. The convex portions can be convex bars, circular bosses, square bosses, conical bosses, etc.

In the above embodiments, the staple strip 2 is made of a biocompatible material. In selective embodiments, the staple strip body 21 and the staple 22 can be made of different materials. For example, in some embodiments, the staple strip body 21 is made of a non-absorbable and non-degradable material such as titanium, titanium alloy, and stainless steel. The staple 22 can be selectively made of a material, which is both biodegradable and biocompatible. The staple 22 can be selectively made of a biocompatible material which is both biodegradable and bioabsorbable material, so that after suturing the staple 22 onto the tissue, subsequent staple removal operations are no longer needed. For example, the staple 22 is made of magnesium, magnesium alloy, biodegradable polymer materials, etc., but the present disclosure is not limited to this. Furthermore, the surface of the staple 22 can also be coated with a biocompatible coating, which is both biodegradable and bioabsorbable. This coating can further improve the hardness of the staple 22 and adjust the degradation rate of the staple 22. The coating can be, for example, an absorbable material coating, such as an L-polylactic acid (PLLA) coating and/or a racemic polylactic acid (PDLLA) coating, but the present disclosure is not limited to this. By adjusting the thickness of the coating, the overall degradation rate of the staple 22 can be adjusted. Alternatively, the coating can be made of a clotting agent that can reduce bleeding during the anastomosis process. In other embodiments, the surface of the staple 22 may be provided with a magnetic coating. When an external magnetic field is applied, the coating is magnetized, which can achieve the effect of enhancing the anastomosis strength. The external magnetic field can be an electromagnetic field, and the magnetic field strength can be adjusted to meet the needs of anastomosis, or the magnetic field can be a permanent magnetic field.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A cartridge assembly comprising:
a staple strip comprising at least one staple strip body and a plurality of staples, wherein each staple is rotatably connected to the staple strip body via a connecting portion;
a cartridge cover jacketed on the staple strip body, wherein the cartridge cover comprises at least one bent portion extending in an axial direction of the cartridge cover, the bent portion is provided with a plurality of staple holes, each staple hole comprises a first hole wall and a second hole wall extending in the axial direction, the first hole wall and the second hole wall are located on different planes, each staple hole is three-dimensional, and the first hole wall is higher than the second hole wall in a height direction.

2. The cartridge assembly of claim 1, wherein the bent portion is connected between an upper plate and a side plate of the cartridge cover, and each staple hole comprises a first section and a second section connected to each other, the first hole wall is located on the upper plate of the cartridge cover, and the second hole wall is located on the side plate of the cartridge cover.

3. The cartridge assembly of claim 2, wherein the first hole wall is parallel to a surface of the side plate of the cartridge cover, and the second hole wall is parallel to a surface of the upper plate of the cartridge cover.

4. The cartridge assembly of claim 2, wherein a highest point of the connecting portion is lower than a highest point of the first hole wall of the staple hole in the height direction; or, a lowest point of the connecting portion is lower than a highest point of the second hole wall of the staple hole in the height direction.

5. The cartridge assembly of claim 2, wherein a projecting area of the connecting portion from the side plate of the cartridge cover at least partially coincides with a projecting area of the staple hole from the side plate of the cartridge cover.

6. The cartridge assembly of claim 2, wherein a lateral distance between the first hole wall and the second hole wall of the staple hole is greater than that between two sides of the staple; wherein a projecting area of the staple from the upper plate of the cartridge cover falls within a coverage range of a projecting area of the staple hole from the upper plate of the cartridge cover.

7. The cartridge assembly of claim 1, wherein a distal end or a proximal end of the second hole wall is provided with a concave arc, and a lowest point of the concave arc is lower than the second hole wall in the height direction.

8. The cartridge assembly of claim 1 further comprising a support member; during a process of rotating each of the staples, at least a part of a side wall of each of the staples simultaneously abuts the support member and an inner wall of a side plate of the cartridge cover.

9. The cartridge assembly of claim 8, wherein each of the staples further comprises a crown portion connected to the connecting portion; after each of the staples is closed and formed, the crown portion is configured to be rotated to a position substantially parallel to the axial direction, and a highest point of the second hole wall is higher than a lowest point of the crown portion.

10. The cartridge assembly of claim 9, wherein the crown portion is provided with a barb, and in an initial state, the second hole wall is higher than the barb.

11. The cartridge assembly of claim 8 further comprising a firing member, wherein the staple strip body is configured to be mounted on one side of the support member, and the staple strip body comprises a first surface away from the support member;
the cartridge cover comprises a second surface arranged relative to the first surface of the staple strip body, and a first gap is formed between the first surface of the staple strip body and the second surface of the cartridge cover;
the firing member is movably arranged at a bottom of the cartridge cover and movable along the axial direction; the firing member comprises a cutting portion, and a highest point of the cutting portion is higher than the first surface of the staple strip body in the height direction.

12. The cartridge assembly of claim 11, wherein a lowest point of the cutting portion of the firing member is lower than the first surface of the staple strip body in the height direction, and the cutting portion of the firing member is configured to be at least partially aligned with the connecting portion in the axial direction.

13. The cartridge assembly of claim 11 further comprising at least one cartridge convex portion, wherein the cartridge convex portion comprises a first portion located between the first surface of the staple strip body and the second surface of the cartridge cover, and a height from an upper surface to a bottom surface of the first portion of the cartridge convex portion is equal to that of the first gap.

14. The cartridge assembly of claim 13, wherein a surface of the support member is provided with at least one second cartridge convex portion, a surface of the second cartridge convex portion away from the support member is higher than the first surface of the staple strip body in the height direction, and the surface of the second cartridge convex portion away from the support member abuts the second surface of the cartridge cover.

15. The cartridge assembly of claim 14, wherein a lateral distance between an inner surface and an outer surface of the first cartridge convex portion is less than that between an inner surface and an outer surface of the staple strip body, and a surface of the staple strip body is provided with at least one mounting hole, wherein the first cartridge convex portion is inserted into the mounting hole; or, the cartridge assembly comprises a plurality of staple strips arranged along the axial direction, and the first cartridge convex portion is configured to be located between the staple strip bodies of adjacent two staple strips.

16. The cartridge assembly of claim 13, wherein the first surface of the staple strip body is provided with at least one third cartridge convex portion, and a surface of the third cartridge convex portion away from the staple strip body abuts the second surface of the cartridge cover; or, the second surface of the cartridge cover is provided with a fourth cartridge convex portion extending towards the staple strip, and a surface of the fourth cartridge convex portion facing the staple strip body abuts the first surface of the staple strip body.

17. A head assembly comprising an anvil and the cartridge assembly according to claim 1, wherein a surface of the anvil facing the cartridge assembly is an anvil surface, and an anvil cutting slot is provided in the anvil, the anvil surface is provided with an anvil convex portion protruding towards the cartridge assembly on at least one side of the anvil cutting slot; a cartridge cutting slot is provided in the cartridge assembly and the bent portion is provided on one side of the cartridge cover close to the cartridge cutting slot.

18. The head assembly of claim 17, wherein the anvil surface is provided with the anvil convex portion on each of two sides of the anvil cutting slot, and at least one cartridge cover is provided on each side of the cartridge cutting slot of the cartridge assembly.

19. The head assembly of claim 17, wherein the head assembly has a first state and a second state respectively; when in the first state, a distal side of the anvil is relatively far from the cartridge assembly, and when in the second state, a distal side of the anvil is relatively close to the cartridge assembly;

when in the second state, a second gap in a height direction is formed between a lowest point of the anvil convex portion and an upper surface of the cartridge cover; a third gap in a width direction is formed between an outer wall of the anvil convex portion and an inner wall of the cartridge cover.

20. A surgical stapler comprising the cartridge assembly according to claim 1.

* * * * *